United States Patent
Ting et al.

(10) Patent No.: US 11,432,733 B2
(45) Date of Patent: Sep. 6, 2022

(54) TISSUE DETECTION DEVICES, SYSTEMS AND METHODS

(71) Applicant: BLOSSOM INNOVATIONS, Waltham, MA (US)

(72) Inventors: Joe Ting, Acton, MA (US); Vincent Zuo, Boston, MA (US); Ben Apollonio, Lunenburg, MA (US); Tania To, Braintree, MA (US); James Wright, Roxbury, MA (US)

(73) Assignee: BLOSSOM INNOVATIONS, Waltham, MA (US)

( * ) Notice: Subject to any disclaimer, the term of this patent is extended or adjusted under 35 U.S.C. 154(b) by 0 days.

(21) Appl. No.: 16/801,060

(22) Filed: Feb. 25, 2020

(65) Prior Publication Data
US 2020/0289021 A1    Sep. 17, 2020

Related U.S. Application Data

(60) Provisional application No. 62/817,914, filed on Mar. 13, 2019.

(51) Int. Cl.
*A61B 5/0538* (2021.01)
*A61B 18/14* (2006.01)
(Continued)

(52) U.S. Cl.
CPC .......... *A61B 5/0538* (2013.01); *A61B 5/0015* (2013.01); *A61B 5/0536* (2013.01);
(Continued)

(58) Field of Classification Search
None
See application file for complete search history.

(56) References Cited

U.S. PATENT DOCUMENTS 3,313,293 A * 4/1967 Chesebrough ....... A61N 1/0502
                                                           600/373
3,682,162 A * 8/1972 Colyer .................... A61M 5/32
                                                           600/373
(Continued)

FOREIGN PATENT DOCUMENTS

| CN | 106061420 B | 12/2021 |
| WO | 2018/200865 | 1/2018 |
| WO | 2018175348 A1 | 9/2018 |

OTHER PUBLICATIONS

Integral, Merriam-Webster.com, https://www.merriam-webster.com/dictionary/integral, printed Aug. 23, 2021, 3 pages (Year: 2021).*

(Continued)

*Primary Examiner* — Matthew Kremer
(74) *Attorney, Agent, or Firm* — Hunton Andrews Kurth LLP

(57) ABSTRACT

An exemplary tissue detection and location identification apparatus can include, for example, a first electrically conductive layer at least partially (e.g., circumferentially) surrounding a lumen, an insulating layer at least partially (e.g., circumferentially) surrounding the first electrically conductive layer, and a second electrically conductive layer circumferentially surrounding the insulating layer, where the insulating layer can electrically isolate the first electrically conductive layer from the second electrically conductive layer. A further insulating layer can be included which can at least partially surrounding the second electrically conductive layer. The first electrically conductive layer, the insulating layer, and the second electrically conductive layer can form a structure which has a first side and a second side disposed opposite to the first side with respect to the lumen, where the first side can be longer than the second side thereby forming a sharp pointed end via the first side at a distal-most portion. The exemplary configuration can be (Continued)

used for (a) determination/detection of a tissue type using impendence of the electrically conductive layers, and/or (ii) determination of a location of at least one portion of the insertion device/apparatus.

35 Claims, 34 Drawing Sheets

(51) Int. Cl.
    *A61B 5/00*         (2006.01)
    *A61B 5/06*         (2006.01)
    *A61B 5/0537*     (2021.01)
    *A61B 5/0536*     (2021.01)
    *A61B 10/02*      (2006.01)
    *A61B 18/00*      (2006.01)
    *A61B 10/04*      (2006.01)

(52) U.S. Cl.
    CPC ............ *A61B 5/0537* (2013.01); *A61B 5/063* (2013.01); *A61B 5/742* (2013.01); *A61B 5/7405* (2013.01); *A61B 5/746* (2013.01); *A61B 10/0283* (2013.01); *A61B 18/14* (2013.01); *A61B 2010/045* (2013.01); *A61B 2018/00077* (2013.01); *A61B 2018/00083* (2013.01); *A61B 2018/00755* (2013.01); *A61B 2018/1427* (2013.01)

(56) References Cited

U.S. PATENT DOCUMENTS

| | | | | |
|---|---|---|---|---|
| 4,469,109 | A * | 9/1984 | Mehl | A61B 10/025 600/566 |
| 4,566,183 | A * | 1/1986 | Bloom | A61B 18/14 174/DIG. 8 |
| 5,279,306 | A * | 1/1994 | Mehl | A61B 10/025 600/566 |
| 5,294,325 | A | 3/1994 | Liu | |
| 5,634,924 | A | 6/1997 | Turkel et al. | |
| 5,997,568 | A | 12/1999 | Liu | |
| 6,315,777 | B1 | 11/2001 | Comben | |
| 6,356,783 | B1 * | 3/2002 | Hubbard, Jr. | A61B 5/0492 600/546 |
| 6,371,943 | B1 | 4/2002 | Racz et al. | |
| 7,862,563 | B1 * | 1/2011 | Cosman | A61B 18/1477 606/41 |
| 8,953,911 | B1 | 2/2015 | Xu et al. | |
| 10,687,730 | B2 | 6/2020 | Kronström et al. | |
| 10,779,804 | B2 | 9/2020 | Kronström et al. | |
| 2002/0042594 | A1* | 4/2002 | Lum | A61B 18/14 604/117 |
| 2004/0143218 | A1 | 7/2004 | Das | |
| 2005/0277829 | A1 | 12/2005 | Tsonton | |
| 2006/0285350 | A1 | 12/2006 | Wang | |
| 2009/0088711 | A1 | 4/2009 | Shelley et al. | |
| 2009/0171304 | A1* | 7/2009 | Cao | A61B 17/3478 604/272 |
| 2010/0204560 | A1 | 8/2010 | Salahieh et al. | |
| 2010/0286507 | A1* | 11/2010 | Paassilta | A61B 5/063 600/424 |
| 2010/0298822 | A1 | 11/2010 | Behnke | |
| 2012/0310315 | A1 | 12/2012 | Savage et al. | |
| 2014/0088371 | A1 | 3/2014 | Vayser et al. | |
| 2014/0133814 | A1 | 5/2014 | Stevens et al. | |
| 2014/0228838 | A1 | 8/2014 | Kirschenman | |
| 2014/0303494 | A1 | 10/2014 | Janicki et al. | |
| 2014/0316254 | A1 | 10/2014 | Eversull et al. | |
| 2015/0209105 | A1 | 7/2015 | Margallo Balbas et al. | |
| 2015/0216442 | A1* | 8/2015 | Lavy | A61B 10/0233 600/547 |
| 2015/0272451 | A1 | 10/2015 | Razavi et al. | |
| 2015/0351670 | A1 | 12/2015 | Vanslyke et al. | |
| 2015/0374915 | A1 | 12/2015 | Hyde et al. | |
| 2016/0029920 | A1 | 2/2016 | Kronstrom et al. | |
| 2016/0066894 | A1 | 3/2016 | Barton-Sweeney et al. | |
| 2016/0081585 | A1 | 3/2016 | Halter | |
| 2017/0049378 | A1 | 2/2017 | Schipper | |
| 2017/0086801 | A1 | 3/2017 | Furlong et al. | |
| 2017/0143201 | A1 | 5/2017 | Claude et al. | |
| 2017/0172618 | A1 | 6/2017 | Erkamp et al. | |
| 2017/0254636 | A1 | 9/2017 | Foster et al. | |
| 2018/0140278 | A1 | 5/2018 | Bromberg et al. | |
| 2018/0250217 | A1 | 9/2018 | Davidson et al. | |
| 2018/0296146 | A1 | 10/2018 | Harttig | |
| 2018/0296197 | A1 | 10/2018 | Kronstrom et al. | |
| 2018/0317896 | A1 | 11/2018 | Kadamus et al. | |
| 2019/0328295 | A1 | 10/2019 | Liu et al. | |
| 2021/0270705 | A1 | 9/2021 | Van Der Zaag et al. | |

OTHER PUBLICATIONS

Integral, www.dictionary.com/browse/integral, 7 pages, printed on Mar. 7, 2022 (Year: 2022).*

Wheeler, D. J. et al., Statistical Tolerance Intervals (1992). Understanding Statistical Process Control. Quality Digest, pp. 1-13 [From the Internet] https://www.qualitydigest.com/inside/statistics-column/stattistical-tolerance-intervals-010416.html.

Rocha, Rafael Dahmer, et al., "Step-by-step of ultrasound-guided core-needle biopsy of the breast: review and technique," Radiol Bras. Jul. 2013/Ago;46(4):234-241.

Covidien, "Principles of Electrosurgery," Boulder CO, pp. 1-28, 2008.

Yun, Joho et al., Micro electrical impedance spectroscopy on a needle for ex vivo discrimination between human normal and cancer renal tissues, Biomicrofluidics 10, 034109, pp. 1-9, (2016).

Yun, Joho et a., "Fabrication of Fine Electrodes on the Tip of Hypodermic Needle Using Photoresist Spray Coating and Flexible Photomask for Biomedical," Journal of Visualized Experiments, Nov. 2017, 129, [From the Internet] https:www.jove.com/video/56622.

Cano, Ivorra et al., Contributions to the measurement of electrical impedance for living tissue ischemia injury monitoring, Doctoral Thesis, Universitat Politècnica de Catalunya, p. 1-20, Feb. 2005.

Abduljabbar, Mohammed H. et al., "Complications of hyaluronic acid fillers and their managements," Journal of Dermatology & Dermatologic Surgery 20 (2016), pp. 100-106.

International Search Report and Written Opinion for International Patent Application No. PCT/US2020/022641 dated Jun. 15, 2020.

International Search Report and Written Opinion for International Patent Application No. PCT/US2020/022614 dated Jul. 1, 2020.

Burgher, Julie M et al., "PhotoPoint photodynamic therapy with local drug delivery eliminates vessel wall cells in arteriovenous graft models," Cardiovascular radiation medicine, ISSN: 1522-1865, vol. 3, Issue: 3-4, pp. 163-168, 2002.

Sepulveda, Abel et al., "Vascular Tumors," Semin Plast Surg. May 2014; 28(2): 49-57.

Schär, Dorothee et al., "Anti-infective therapy of peri-implantitis with adjunctive local drug delivery or photodynamic therapy: six-month outcomes of a prospective randomized clinical trial, Clinical Oral Implants Research," vol. 24(1), pp. 104-110.

Selfridge, Alan et al., "Wideband Spherically Focused PVDF Acoustic Sources for Calibration of Ultrasound Hydrophone Probes," IEEE Transactions on Ultrasonics, Ferroelectrics, and Frequency Control, vol. 47, No. 6, Nov. 2000.

Ribatti, Domenico, et al., "Angiogenesis and Melanoma," Cancers 2010, 2, 114-132.

Pelras, Théophile et al., "Transparent Low Molecular Weight Poly(Ethylene Glycol) Diacrylate-Based Hydrogels as Film Media for Photoswitchable Drugs," Polymers 2017, vol. 9, p. 639 (2017).

Liberman, Laura, "Percutaneous Imaging-Guided Core Breast Biopsy: State of the Art at the Millennium," AJR:174, May 2000.

(56) References Cited

OTHER PUBLICATIONS

Advisory Action for U.S. Appl. No. 17/193,798 dated Mar. 4, 2022.
Non Final Office Action for U.S. Appl. No. 17/438,816 dated Feb. 18, 2022.

* cited by examiner

705

2191

2192    2193    2194

TISSUE DETECTION DEVICES, SYSTEMS AND METHODS

CROSS-REFERENCE TO RELATED APPLICATION(S)

This application relates to and claims priority from U.S. Patent Application No. 62/817,914, filed on Mar. 13, 2019, the entire disclosure of which is incorporated herein by reference.

FIELD OF THE DISCLOSURE

The present disclosure relates generally to a detection or sensing of an animal or human tissue type, and more specifically, to exemplary embodiments of exemplary apparatus, devices and systems, which can be integrated into one or more insertion devices (e.g., including but not limited to a needle, cannula, etc.), for determining a tissue or fluid type prior to (i) an injection of any substance or material (e.g., drugs, biologics, filler, therapeutics, cellular materials, cells, genetic materials, stem cells, immunotherapy agents, etc.) and/or (i) an aspiration of fluids or collection of materials or tissue (e.g., core biopsy) from a body via such insertion apparatus, and to exemplary methods for manufacturing such insertion apparatus and/or sensing or determining the tissue type upon the insertion thereof.

BACKGROUND INFORMATION

When performing surgery or procedure on a animal or human subject, or injecting any substance(s) and/or or material(s), including but not limited a pharmacological agents (e.g., a drug), filler substances, biological and non biological fillers, therapeutics, tissue or cellular material, stem cells, genetic materials, immunotherapy agents, etc. into an animal or human subject, it can be beneficial to inject the material into a particular tissue of the subject (e.g., certain blood vessels, fat, muscle, etc.) in some applications. It can also be important or beneficial to not inject the materials into certain tissue or lumen in the subject (e.g., certain blood vessels, etc.), in some applications, while being beneficial to inject such materials in such tissue or lumens in other applications. There are a number of commercially available non-invasive visualization systems (including ultrasound and optical visualization devices, etc.) to help identify and access specific structures such as veins or arteries (phlebotomy, IV, etc.). One example is the AccuVein which incorporates an infrared light source and detector which provide visualization of shallow veins. There are, however, no known technologies which are integrated with such access devices capable of specifically sensing or tissue changes or detecting blood vessels for the purpose of vessel targeting or avoidance.

Various non-insertion technologies exist for related applications, for example: (i) detecting blood vessels for the purpose of injection or blood collection, and (ii) detecting when a needle has penetrated a specific type of tissue (e.g., spinal space or other). However, there are no known insertion devices/arrangements that integrate sensing electrodes that facilitate rapid or real-time sensing/detection of different tissue types, while also facilitating an injection of substances or materials into a body and/or an aspiration of fluids or collection of material, cells or tissues from the body, such as, e.g., pharmacological agents, fillers, biologics, therapeutics, cellular materials, stem cells, genetic materials, immunotherapy agents, substances, etc., for example, with no manipulation of the insertion devices/arrangements.

One company, Injeq, created an IQ-Needle, which is a needle that uses electrical impedance spectroscopy to detect various tissue types, for example, to detect when the needle has penetrated spinal fluid. The needle incorporates two electrodes; one electrode is incorporated into a needle, and the other is incorporated into a stylet located inside the needle. After the target location has been detected, the stylet needs to be removed and then a syringe or other device must be connected to the needle before the procedure (e.g., injection or fluid collection) can begin. The IQ-Needle is shown and described in U.S. Patent Publication No. 2016/0029920, the entire disclosure of which is incorporated herein by reference in its entirety. Injeq has also developed a biopsy needle that uses the same approach. (See, e.g., U.S. Patent Publication No. 2018/0296197, the entire disclosure of which is incorporated herein by reference in its entirety).

Another prior system includes a sensing needle incorporating interdigitated, co-planar, electrodes on the surface for identifying different tissues using electrical impedance spectroscopy. The electrodes are deposited directly on the needle using conventional printed circuit board fabrication techniques. In such system, however, the needle is closed. Thus, the needle can only be used for sensing, and not for injecting an agent into a subject. Additionally, the needle is tethered to an analyzer used to determine the tissue type. Finally, since the electrodes are on the outer circumferential surface of the needle, the electrodes are not co-located with the tip. Therefore, the measurements from the electrodes do not reflect the conditions at the tip.

Additionally, many minimally invasive procedures involve devices, such as needles or catheters, which use external imaging to guide devices within the body. Imaging techniques include ultrasound, X-rays, magnetic resonance imaging (MRI), etc. Ultrasound imaging has been shown to be an effective guidance technology, although it provides only a two-dimensional (2D) image with limited information and somewhat poor needle visualization (See, e.g., Rocha et al., "Step-by-step of ultrasound-guided core-needle biopsy of the breast: review and technique," Radiol Bras. 2013 July/Ago; Vol. 46(4), pages 234-241). Further, X-ray or computerized tomography (CT) scans expose both the clinician and the subject to unwanted radiation. Thus, X-ray, CT, and MRI equipment is typically centralized with scheduling limitations. It is indeed difficult to provide a three-dimensional (3D) location of the tissue using the existing technology, and also limiting the negative effects of the devices that are needed to obtain the location.

Thus, it may be beneficial to provide exemplary apparatus, devices and systems, which can be integrated into a one or more insertion devices (e.g., including but not limited to a needle, cannula, catheter, etc.), for:
  determining a tissue type prior to and/or during (i) an injection of any substance or material (e.g., such as, e.g., pharmacological agents, biologics, fillers, therapeutics, cellular materials, stem cells, genetic materials, immunotherapy agents, substances, etc.) and/or (ii) an aspiration of fluids, substances, materials, cells, or tissues from a body via such insertion apparatus, and to exemplary methods for manufacturing such insertion apparatus and/or determining the tissue type upon the insertion thereof, and
  determining and/or inferring a position of a tip of an insertion apparatus/device in three-dimensional space, e.g., using some of the same components which can be used for the used for the tissue type determination which can overcome at least some of the deficiencies described herein above.

SUMMARY OF EXEMPLARY EMBODIMENTS

To that end, such exemplary apparatus, devices and systems can be provided according to exemplary embodiments of the present disclosure which can include and/or utilize an insertion device/apparatus.

To that end, an exemplary insertion apparatus/device according to an exemplary embodiment of the present disclosure can include, for example, a first electrically conductive layer at least partially (e.g. circumferentially) surrounding a lumen, an insulating layer at least partially (e.g. circumferentially) surrounding the first electrically conductive layer, and a second electrically conductive layer at least partially (e.g. circumferentially) surrounding the insulating layer, where the insulating layer can electrically isolate the first electrically conductive layer from the second electrically conductive layer. A further insulating layer can be included which can at least partially (e.g. circumferentially) surrounding the second electrically conductive layer. The first electrically conductive layer, the insulating layer, and the second electrically conductive layer can form a structure which has a first side and a second side disposed opposite to the first side with respect to the lumen, where the first side can be longer than the second side thereby forming a sharp pointed end via the first side at a distal-most portion of the insertion apparatus/device. The first electrically conductive layer, the insulating layer, and the second electrically conductive layer can form a structure that can be beveled to form a sharp pointed end at a distal-most portion of the insertion apparatus/device.

In some exemplary embodiments of the present disclosure, the first electrically conductive layer, the insulating layer, and the second electrically conductive layer can form a shaft of the insertion apparatus/device. The first electrically conductive layer, the insulating layer, and the second electrically conductive layer can form a structure that can extend distally from a hub. A barrel can be connected to the hub and a plunger can be configured to be inserted into the barrel. The first electrically conductive layer can be configured to transmit and/or receive an electrical signal (e.g., a first electrical signal), and the second electrically conductive layer can be configured to transmit and/or receive the same or different electrical signal (e.g., the first and/or the second electrical signal), and a communication device(s) can be configured transmit information related to the electrical signal(s). The communication device(s) can be embedded in one of (i) a hub of the insertion apparatus/device, or (ii) a barrel of the insertion apparatus/device.

In certain exemplary embodiments of the present disclosure, the first electrically conductive layer can be configured to transmit and/or receive the electrical signal (e.g., a first electrical signal), and the second electrically conductive layer can be configured to transmit and/or receive the same or different electrical signal (e.g., the first or the second electrical signal), and a hardware processing arrangement can be configured to receive information related to the electrical signal(s), determine an impedance based on the information, and determine a tissue or fluid type based on the impedance. An audible arrangement can be configured to emit a sound based on the determined tissue or fluid type. The processing arrangement can be embedded in (i) a hub of the insertion apparatus/device, and/or (ii) a barrel of the insertion apparatus/device. Alternatively, the processing arrangement may be removably detachable from the hub or barrel. The lumen can be configured to (i) have a pharmacological agent injected therethrough, or (ii) have a biopsy sample obtained therethrough.

In another exemplary aspect of the present disclosure, the insertion apparatus/device can include a needle device, a cannula and/or other insertion configuration which has the first electrically conductive layer, the lumen, the insulating layer and the second electrically conductive layer.

According to still another exemplary embodiment of the present disclosure, an exemplary insertion apparatus/device can be provided which includes, for example, a hub and a shaft extending from the hub and surrounding a lumen, where the shaft can include an outer surface having an electrode(s) formed thereon or therein. A barrel can be connected to the hub and a plunger can be configured to be inserted into the barrel. A communication device(s) can be embedded in at least one of (i) the hub, (ii) the barrel, or (iii) a separate package which is mechanically and electrically connected to the hub or barrel. The electrode(s) can be configured to obtain an electrical signal, and a hardware processing arrangement can be embedded in (i) the hub, (ii) the barrel, or (iii) a separate package which is mechanically and electrically connected to the hub or barrel, where the hardware processing arrangement can be configured to receive information related to the electrical signal, determine an impedance based on the information, and determine a tissue type based on the impedance. The shaft can includes an insulating layer at least partially (e.g., circumferentially) surrounded by the outer surface and an electrically conductive layer at least partially (e.g., circumferentially) surrounded by the insulating layer, where the electrically conductive layer can form a further electrode. The electrode(s) can be integrated into the shaft.

Further, an exemplary insertion apparatus/device can include, for example, a hub and a shaft surrounding a lumen, where the shaft can include at least two non-removable electrodes. A processing arrangement can be configured to receive information related to (i) a first electrical signal obtained using a first one of the at least two non-removable electrodes and (ii) a second electrical signal obtained using a second one of the at least two non-removable electrodes, determine an impedance based on the information, and determine a tissue type based on the impedance.

According to still another exemplary aspect of the present disclosure, the insertion apparatus/device can include a needle device, a cannula and/or other insertion configuration which include(s) the hub and the barrel.

An exemplary method of determining a type of a tissue(s) of a subject(s) using an insertion apparatus/device can be provided. For example, according to such exemplary method, it is possible to, for example, receive a first electrical signal using a first electrically conductive layer that at least partially (e.g. circumferentially) surrounds a lumen of the needle, receive a second electrical signal using a second electrically conductive layer that at least partially (e.g. circumferentially) surrounds the first electrically conductive layer, determine an impedance based on the first and second electrical signals, and determine the type based on the impedance, e.g., by comparing a magnitude of the impedance or a phase of the impedance with predetermined values at one or more frequencies. The first electrically conductive layer can be isolated from the second electrically conductive layer using an insulating layer(s). Substances or materials into a body and/or an aspiration of fluids from the body, such as, e.g., pharmacological agents, biologics, fillers, therapeutics, cellular materials, stem cells, genetic materials, immunotherapy agents, etc. can be administered to the subject(s)

through the lumen or a biopsy sample and/or any other substance of fluid can be obtained or removed from the subject(s) through the lumen.

Additionally, an exemplary method for determining a type of a tissue(s) of a subject(s) using an insertion device/apparatus can be provided. With such exemplary method, it is possible to, for example, receive an electrical signal(s) using an electrode(s) formed on or in an outer surface of a shaft of the insertion device/apparatus, determine an impedance based on the at least one electrical signal, and determine the type based on the impedance by comparing a magnitude of the impedance or a phase of the impedance with predetermined values at one or more frequencies. Substances or materials, such as pharmacological agents, biologics, fillers, therapeutics, cellular materials, stem cells, genetic materials, immunotherapy agents, substances, etc. can be administered to the subject(s) through the lumen of the insertion device/apparatus when a particular type is determined as being reached by a particular portion of the insertion device/apparatus or a biopsy sample can be obtained from the subject(s) through the lumen based on the determination. Alternatively and/or in addition, it is possible to aspirate fluid or other material from the sample using the determination of the type of the tissue reached by a particular portion of the insertion device/apparatus.

Further, an exemplary method of determining a type of a tissue(s) of a subject(s) using an insertion device/apparatus can be provided. With such exemplary method, it is possible to, for example, receive at least two electrical signals using at least two non-removable electrodes integrated into the insertion device/apparatus, determine an impedance based on the at least two electrical signals, and determine the type based on the impedance by comparing a magnitude of the impedance or a phase of the impedance with predetermined values at one or more frequencies. Substances or materials, such as, e.g., pharmacological agents, fillers, biologics, therapeutics, cellular materials, stem cells, genetic materials, immunotherapy agents, etc. can be administered to the subject(s) through the lumen of the insertion device/apparatus when a particular type is determined as being reached by a particular portion of the insertion device/apparatus or a biopsy sample can be obtained from the subject(s) through the lumen based on such determination. Alternatively and/or in addition, it is possible to aspirate fluid or other material from the sample using the determination of the type of the tissue reached by a particular portion of the insertion device/apparatus.

An exemplary tissue and/or fluid detection apparatus can include, for example, an insertion device/apparatus (e.g., which can be a needle device, a cannula and/or other insertion configuration) that can be configured inject substances or materials, such as, e.g., pharmacological agents, biologics, fillers, therapeutics, cellular materials, stem cells, genetic materials, immunotherapy agents, substances, etc. into a subject and/or remove a biopsy sample and/or other fluid, tissue, cells or material from the subject. The needle can be used to receive one or more electrical signals, which can be used to determine an impedance. The exemplary insertion device/apparatus can include a first electrically conductive layer at least partially (e.g. circumferentially) surrounding a lumen, an insulating layer at least partially (e.g. circumferentially) surrounding the first electrically conductive layer, and a second electrically conductive layer at least partially (e.g. circumferentially) surrounding the insulating layer, where the insulating layer can electrically isolate the first electrically conductive layer from the second electrically conductive layer. A further insulating layer can be included which can at least partially (e.g. circumferentially) surrounding the second electrically conductive layer.

In some exemplary embodiments of the present disclosure, the exemplary insertion device/apparatus can include a hub and a shaft extending from the hub and surrounding a lumen, where the shaft can include an outer surface having an electrode(s) formed thereon or therein. In certain exemplary embodiments of the present disclosure, the exemplary needle can include a hub and a shaft surrounding a lumen, where the shaft can include at least two non-removable electrodes. A communication device can be used to transfer/transmit information (e.g., wired or wirelessly) related to the electrical signals to a computer processing device. The processing device, which can be a mobile apparatus (e.g., phone, tablet, etc.), can be used to determine the impedance based on the electrical signals, and can also sense changes in the tissues and/or determine a tissue or fluid type based on the impedance.

As described above, the exemplary tissue detection and/or position indication system/apparatus can include a single insertion device/apparatus (e.g., needle, cannula, etc.). However, the exemplary tissue detection and/or position indication system/apparatus can include a plurality of such devices/apparatuses (e.g., needles, cannula, etc., and/or any combination thereof). Each tissue detection system/apparatus in the array thereof s can have, the same or similar electrode design/structure (e.g., same or similar design of the various exemplary electrode designs/structures described herein). Alternatively or in addition, each tissue detection and/or position indication system/apparatus in the array can have a different design/structure, or a subset of the needles can have one design/structure while another subset can have a different design/structure. Each tissue detection and/or position indication system/apparatus in the exemplary array of needles can perform the exemplary tissue detection as described herein, and each tissue detection system/apparatus can also perform a further function of, e.g., the administering of substances or materials, such as, e.g., pharmacological agents, biologics, fillers, therapeutics, cellular materials, stem cells, genetic materials, immunotherapy agents, etc. to the subject and/or the removal of a biopsy sample and/or other materials or fluid from the subject (all at the specific tissue based on the determination of a particular tissue of the subject. Thus, one or more of such insertion devices in the exemplary array thereof can perform the tissue detection, while one or more other needles can perform the injection or aspiration functions.

The exemplary array of the insertion devices can also be used to increase the accuracy of the tissue detection and/or position indication by increasing the number of the electrodes that are used to determine the impedance. Additionally or alternatively, a comparison of the impedance between insertion devices in the array can also be used to determine the tissue type. According to another exemplary embodiment of the present disclosure, a method can be provided for determining a type of at least one tissue of at least one subject or if an orifice of the tissue has been reached using an insertion arrangement (e.g., a needle arrangement). For example, it is possible to (i) insert the insertion arrangement into at least one portion of the subject to reach the tissue; (ii) receive a first electrical signal using a first electrically conductive layer that at least partially surrounds (e.g., circumferentially) a lumen of the insertion arrangement; (iii) receive a second electrical signal using a second electrically conductive layer that at least partially surrounds (e.g., circumferentially) the first electrically conductive layer; (iv) determine an impedance based on the first and second electrical signals; and (v) determine whether the type or the orifice of the at least one tissue has been reached based on the impedance by comparing at least one of a magnitude of the impedance or a phase of the impedance with predetermined values at one or more frequencies. It is also possible to electrically isolate the first electrically conductive layer from the second electrically conductive layer using at least one insulating layer. Further, it is possible to (i) administer a pharmacological agent to the subject through the lumen, and/or (ii) obtain a biopsy sample from the at least one subject through the lumen.

According to another exemplary embodiment of the present disclosure a similar method can be provided for determining a type of at least one tissue of at least one subject or if an orifice of the tissue has been reached using an insertion arrangement. For example, it is possible to (i) insert the insertion arrangement into at least one portion of the at least one subject to reach the tissue; (ii) receive at least one electrical signal using at least one electrode formed on or in an outer surface of a shaft of the insertion arrangement; (iii) determine an impedance based on the at least one electrical signal; and (iv) determine whether the type or the orifice of the at least one tissue has been reached based on the impedance by comparing at least one of a magnitude of the impedance or a phase of the impedance with predetermined values at one or more frequencies. It is further possible to (i) administer a substance, material or pharmacological agent to the at least one subject through a lumen of the needle or cannula, and/or (ii) obtain a biopsy sample from the at least one subject through the lumen.

According to a still exemplary embodiment of the present disclosure, a method can be provided for determining a type of at least one tissue of at least one subject or if an orifice of the tissue has been reached using an insertion arrangement (e.g., a needle arrangement). With the exemplary method, it is possible to (i) insert the insertion arrangement into at least one portion of the subject to reach the tissue; (ii) receive at least one electrical signal (e.g., and possible at least two electrical signals) using at least two non-removable electrodes integrated into the insertion arrangement; (iii) determine an impedance based on the electrical signal(s); and (iv) determining whether the type or the orifice of the tissue has been reached based on the impedance by comparing at least one of a magnitude or a phase of the impedance with at least one predetermined value of at least one frequency. Similarly to the previously-described exemplary embodiments, it is further possible to (i) administer a pharmacological agent to the subject through a lumen of the insertion arrangement, and/or (ii) obtain a biopsy sample from the subject through the lumen.

All of the above-described exemplary embodiments can be utilized to, e.g., (i) deliver a composition into the tissue of the subject or an orifice of the tissue, and/or (ii) extract material or a fluid from at least one tissue of at least one subject or an orifice of the at least one tissue using an insertion device, e.g., at a particular location of the tissue corresponding a type of the tissue.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1A:
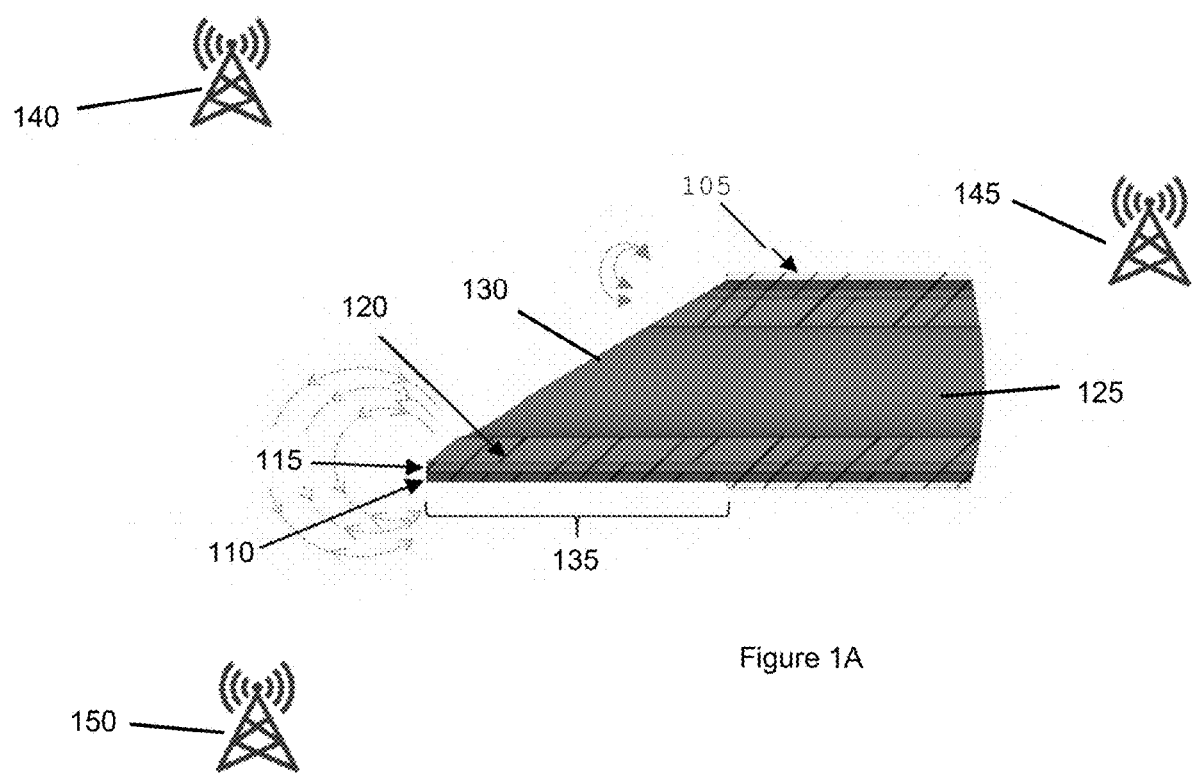
FIG. 1A is an exemplary diagram of a close-up cross-sectional view of a distal end of an exemplary insertion device/apparatus (e.g., a needle) which illustrates the ability of the device/apparatus to sense at the leading edge or tip according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary embodiments of the present disclosure may be further understood with reference to the following description and the related appended drawings. In particular, the exemplary embodiments of the present disclosure relate to at least one insertion device/apparatus (which can be an array thereof) for use in determining a tissue or fluid type. Such determination can be made prior to the injection of a drug. Tissue type can include, but is not limited to, dermis, fat, muscle, skin, bone, nerves, muscle, eye tissue, organ tissue, teeth, etc. Fluids include blood, synovial fluid, lymph fluid, etc. The exemplary embodiments are described with reference to an exemplary insertion device/apparatus, it should be abundantly clear the exemplary embodiments of the present disclosure may be implemented on other insertion and/or injection devices for use in injecting substances into the body of a subject and/or removing substances and/or materials therefrom, including but not limited cannulas, catheters, etc. As used herein, the exemplary insertion device/apparatus can be used on a person (e.g., a human). However, the exemplary insertion device/apparatus can also be used for other subjects including, but not limited to, animals, or other various species.

In still a further exemplary embodiment of the present disclosure, the exemplary insertion device/apparatus can be used to determine or infer a position of a tip thereof in three-dimensional space, e.g., using some of the same components used for the used for the tissue detection.

It should also be understood that any reference to a needle, needle apparatus, etc. according to various exemplary embodiments of the present disclosure described herein also includes, and equally applicable to, other insertion devices for providing and/or extracting substances and/or materials to and from a body, including but not limited to cannulas, endoscopes, laparoscopes, etc.

The exemplary apparatus can utilize, for example, electrical impedance to selectively determine when at least one insertion device (e.g., a needle) has been introduced into a specific type of tissue (such as a blood vessel—e.g., an artery or vein, or into a tissue such as, e.g., fat). The exemplary apparatus can operate utilizing an alternating voltage applied to two or more electrodes located on the apparatus, which can be used to measure the resulting current. Such impedance can be determined from, e.g., the ratio between the voltage and current, and can be, e.g., a complex number (e.g., includes real and imaginary components). The calculated electrical impedance can vary with the frequency and the tissue type. Various exemplary characteristics of the measured impedance (e.g., magnitude and angle as a function of frequency, etc.) can be used to determine tissue type. Such determination can be performed using the exemplary system, device and computer-accessible medium with the use of a processor executing a program that can utilize the information/data associated with the ratio of the voltage, current, etc. as well as other values and information.

In one exemplary embodiment of the present disclosure, the exemplary apparatus, devices and/or systems can be used to measure the impedance at the tip of an insertion device/apparatus (such as, e.g., needle, cannula, endoscope, laparoscope, a hypodermic needle, etc.), and can determine when the tip of the insertion device/apparatus is located within a specific type of tissue or orifice without any alteration to current clinical practice. In this exemplary manner, a medical professional can determine the location of the insertion device/apparatus (e.g., the tissue type) prior to injecting an agent into the subject. Once the correct tissue type for depositing the agent has been determined, the medical professional can introduce (e.g., inject) the agent into the subject. No stylet or other component is needed in order to determine the tissue type. Additionally, the exemplary apparatus can provide an audible, tactile and/or visual alert based on the tissue type.

The exemplary apparatus can include, or can be connected to, for example, a display screen which can intermittently or continuously provide the medical professional or any person inserting the exemplary insertion device/apparatus the information regarding the determined tissue or fluid type based on the determined electrical impedance. For example, when the medical professional first introduces the insertion device/apparatus into the subject, the display can indicate the first tissue or fluid type the insertion device/apparatus is inserted into. As the medical professional pushes the insertion device/apparatus further into the subject, the display device can change as the tissue or fluid type changes. Such change can include providing different colors, shapes, visual indicators, etc. Once the correct or specific tissue or fluid type has been determined as being reached (e.g., based on a visual indication to the medical professional), the medical professional can cease pushing the insertion device/apparatus, and inject any material or substance into the subject at the location of the tip of the insertion device/apparatus, and/or extract any material or substance therefrom. Alternatively, or in addition, the exemplary apparatus can be programmed based on a particular impedance value or tissue or fluid type (e.g., a tissue or fluid type selected by the medical professional to inject the agent into), and an audible alert can sound once the exemplary apparatus has determined the selected impedance value or tissue or fluid type. The audible or light indicator alert can also be programmed to provide a variable tone or light to represent passage through various tissues or fluids, for example, with a frequency that varies with impedance. Through the present disclosure, the terms materials and/or substance are understood to include a pharmacological agent (e.g., a drug), biologics, fillers, therapeutics, cellular materials, stem cells, genetic materials, immunotherapy agents, etc., but certainly not limited thereby.

The exemplary apparatus, devices and systems can include a fully open center lumen, which can facilitate the insertion device/apparatus to be used to deliver any material, substance and/or agent, as well as for, collection, or introduction of other devices (e.g., medical devices) through the lumen. Thus, the exemplary apparatus, devices and systems can be comparable to standard hypodermic needles which are generally characterized by their internal diameter. Further, the exemplary insertion device/apparatus can be fully integrated and tuned to sense specific tissues. For example, a particular insertion device/apparatus can be used for a particular tissue (e.g., the insertion device/apparatus can be tuned to specific frequencies to detect a single type of tissue by reviewing the magnitude and/or phase components of the impedance). The exemplary angle of the tip and/or the width of the insertion apparatus/device described for the exemplary embodiments can be provided and/or fabricated based on various different characteristics of the tissue into which the exemplary insertion device/apparatus is inserted. With respect to the tissue type determination, this can facilitate the electronics of the exemplary apparatus, devices and systems to determine the impedance to be simplified since the exemplary apparatus, devices and systems do not need to obtain a complete spectra, as the exemplary apparatus, devices and systems would only preferably obtain the spectra for the particular tissue type. The exemplary electrodes can be applied using a spray or deposition process, as discussed below. The resulting structure can then be used to produce the exemplary insertion device using conventional grinding and insertion device/apparatus fabrication processes. Additionally, the inner electrode can include the base body of the insertion device/apparatus itself. Two, three, or more electrodes can then be provided by applying additional layers to the insertion device/apparatus. As discussed herein, the exemplary angle of the tip and/or the width of the insertion apparatus/device described for the exemplary embodiments can be provided and/or fabricated based on various different characteristics of the tissue into which the exemplary insertion device/apparatus is inserted.

The exemplary apparatus can be used in the field of a filler injection, including but not limited to a facial filler injection, etc. For example, an injection of a filler into an artery can cause a partial or total vessel occlusion which can lead to tissue necrosis. (See e.g., Reference 6). To address this problem, an exemplary insertion and guidance device/apparatus according to an exemplary embodiment of the present disclosure can provide feedback to a clinician or a medical professional indicating that the tip or opening of such insertion device/apparatus is provided in a blood vessel. In this manner, the medical professional can avoid dispensing the filler into any blood vessel, including, e.g., artery, vein, capillary, etc. Then, occlusions created by certain materials and/or substance (e.g., fillers) injected into a blood vessel (e.g., an artery, a vein, etc.) can be cleared. Such materials and/or substances can include hyaluronic acid. Hyaluronidase is an enzyme that can be used to dissolves hyaluronic acid. Occlusions detected in a timely manner can be cleared by injecting hyaluronidase. An exemplary perfusion detection apparatus can provide an alert that there is an occlusion such that action can be taken before extensive cell death occurs.

For example, the exemplary fillers can include, but certainly not limited to, absorbable or temporary materials (e.g., Collagen, Hyaluronic acid, Calcium hydroxylapatite, Poly-L-lactic acid (PLLA)), non-absorbable or permanent materials (e.g., Polymethylmethacrylate beads (PMMA microspheres)), as well as other materials. Various FDA-approved fillers can be as follows: Restylane Lyft with Lidocaine, Revanesse Versa, Revanesse Versa+, Rha 2, Rha 3, Rha 4, Juvederm Vollure XC, Restylane, Refyne, Restylane Defyne, Juvederm Volbella XC\, Radiesse, Restylane Silk, etc.

FIG. 1A shows an exemplary diagram of an exploded cross-sectional side view of a distal end of an exemplary insertion device/apparatus (e.g. needle) according to an exemplary embodiment of the present disclosure. As shown in FIG. 1A, the exemplary insertion device/apparatus can include a needle 105 incorporating two or more, non-planar, concentric conductive electrodes (e.g., electrodes 110 and 120). One of the electrodes (e.g., electrode 110), can be formed from a conductive coating on or in a surface of the insertion device/apparatus. The use of two or more, non-planar, concentric conductive electrodes can leave center lumen 125 open for delivery, collection, or introduction of fluids or other substances or devices. The exemplary insertion device/apparatus can be of any size as required to inject a pharmaceutical agent, or to introduce a minimally invasive device such as a guidewire or catheter through opening 130.

The exemplary electrodes can have different forms and/or configurations. For example, a portion of the insertion device/apparatus itself (e.g., a portion of the surface of the insertion device/apparatus) can act as one of the electrodes. A second electrode can then be fabricated in-situ and/or pre-fabricated, and then placed on the surface of the insertion device/apparatus. The two electrodes can then be used to measure impedance at the tip of the insertion device/apparatus (e.g., for the determination of the tissue type as discussed herein).

As shown in FIG. 1A, center lumen 125 can be surrounded by electrode 120, which can form an internal portion and/or surface of the insertion device/apparatus itself. An insulative coating 115 (e.g., made of polyimide or any other suitable material, such as polyamide, for example) can surround electrode 120, e.g., outwardly radially. Electrode 110 can then be formed around on insulative coating 110. Thus, insulative coating 115 can be used to electrically isolate electrodes 110, 120 from one another. A second insulative coating, e.g., can surround electrode 110, to isolate electrode 110, except for, e.g., an uninsulated portion 135 of electrode 110.

Figure 1B:
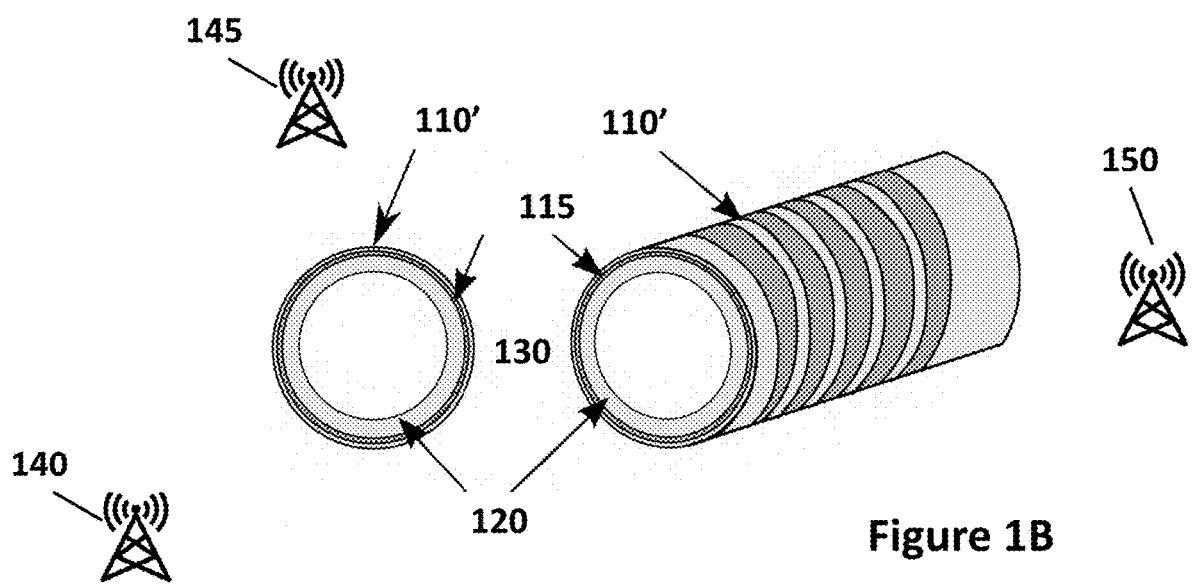
FIG. 1B are a set of exemplary diagrams of cut-away view and a close-up cross-sectional view of a distal end of an exemplary insertion device/apparatus according to another exemplary embodiment of the present disclosure.

According to another exemplary embodiment of the present disclosure, another exemplary insertion device/apparatus can be provided, as shown in FIG. 1B. Indeed, the same exemplary portions/components of the exemplary insertion device/apparatus illustrated in FIG. 1A are labeled with the same numerals in FIG. 1B. Similarly to the exemplary embodiment described herein that provides the three-dimensional location of the tip of the exemplary insertion device shown in FIG. 1A, the exemplary apparatus of FIG. 1B also can use alternating current applied to the exemplary electrodes to determine and/or infer a three-dimensional position of the tip of the exemplary apparatus. Nonetheless, instead of providing electrode 110 which circumferentially surrounds insulating layer 115, masking can be used to produce and/or provide helical-patterned and/or other exemplary patterned structures which define an outer conductive patterned layer 110'. Such exemplary use of the helical-patterned outer conductive layer can improve the transmission of the radiation and/or detection thereof by antennas 140, 145, 150 to facilitate an improved three-dimensional position detection of the tip of the exemplary insertion device. For example, referring again to FIG. 1B, alternating current can be transmitted via the conductive/electrical channels of the device (e.g., internal thereto and/or provided on a surface thereof) to reach helically-patterned outer conductive layer (e.g., electrode) 110' and/or inner conductive base (e.g., inner electrode) 120 so as to generate an electromagnetic field. Such electric field generated by patterned layer (e.g., concentric electrodes) 110' can be detected by antennas 140, 145, 150.

Figure 1C:
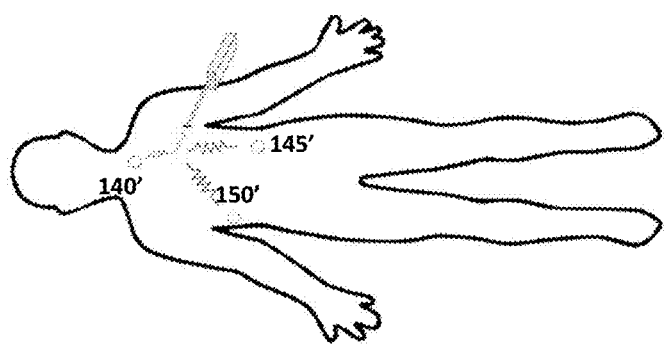
FIG. 1C is a top view of an exemplary application of the exemplary insertion device/apparatus provided on a body according to yet another exemplary embodiment of the present disclosure.

The exemplary insertion device/apparatus shown in FIG. 1B is illustrated in operation in FIG. 1C. In particular, exemplary concentric electrodes 110' illustrated in FIG. 1C facilitate locating the tip of the exemplary insertion device in a three-dimensional space, as discussed herein. This can be done by using, e.g., static current, alternating current and/or another energy or radiation which can include the determination of impedance at the tip. It is also possible to utilize a constant current with the exemplary electrodes 110, 110', 120. For example, constant or alternating current can be applied and/or utilized. For example, the relative distance of the tip to antenna's 140, 145, 150 can be measured due to the current emission. In addition or alternatively, it is possible to provide other surface electrodes 140', 145', 150' placed at different locations on the body to measure current and infer the effective resistance and relative position from the tip to each electrode, e.g., in a three-dimensional space. In addition and/or alternatively, these exemplary electrodes 140', 145', 150' placed at different locations on the body can be used to measure the magnitude of the current which can decrease as a function of distance and resistance/impedance. Thus, using such electrodes 140', 145', 150', it is possible to triangulate the position of the tip in the three-dimensional space.

Figure 2:
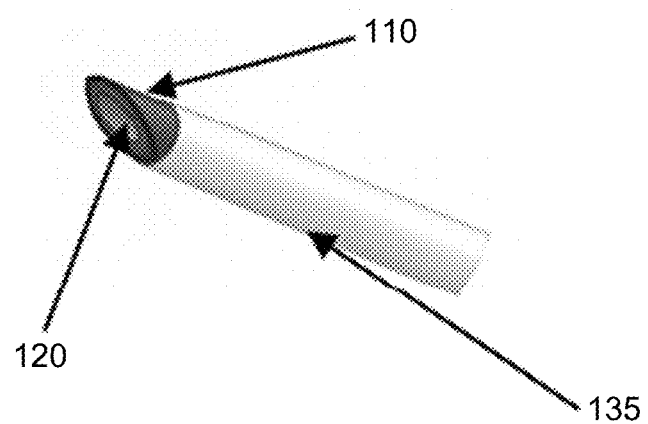
FIG. 2 is further exemplary diagram of an elevation view of the distal end of the exemplary insertion device/apparatus according to an exemplary embodiment of the present disclosure.

FIG. 2 shows a further perspective view of an exemplary diagram of a distal end of the exemplary insertion device/apparatus according to an exemplary embodiment of the present disclosure. As shown in FIG. 2, the insertion device/apparatus can include a needle 120 that can act as one of the electrodes 120, while multiple internal (to needle) coatings are used to produce a second electrode using sequential spray processes (e.g., as described below) to provide—internally to needle—an insulating layer, a second conductive layer, and a selective insulating layer 135 which exposes a discrete part of the outer conductive layer. The electrical current can follow the shortest possible path from one electrode to the other, (e.g., at the very tip). There can also be some contribution from the capacitive coupling through the insulating coating.

For the function of detecting/determining tissue or fluid types, based on the frequencies of interest (e.g., the frequency used to detect the tissue or fluid type), the outer insulating coating can be optional, although it can be used to provide protection for the outer conductive coating and/or lubrication to ease the insertion of needle 120.

The exemplary insertion device/apparatus can include more than two layers (e.g., more than two insulating and conducting layers). For example, additional layers can be applied to produce additional electrodes. In certain exemplary applications, it can be beneficial to utilize more than two electrodes to sense, detect and/or identify fluids or tissues, for example, when the impedance of the fluid/tissue can be lower than the impedance of the sensing electrodes themselves. (See e.g., Reference 5).

Figure 3:
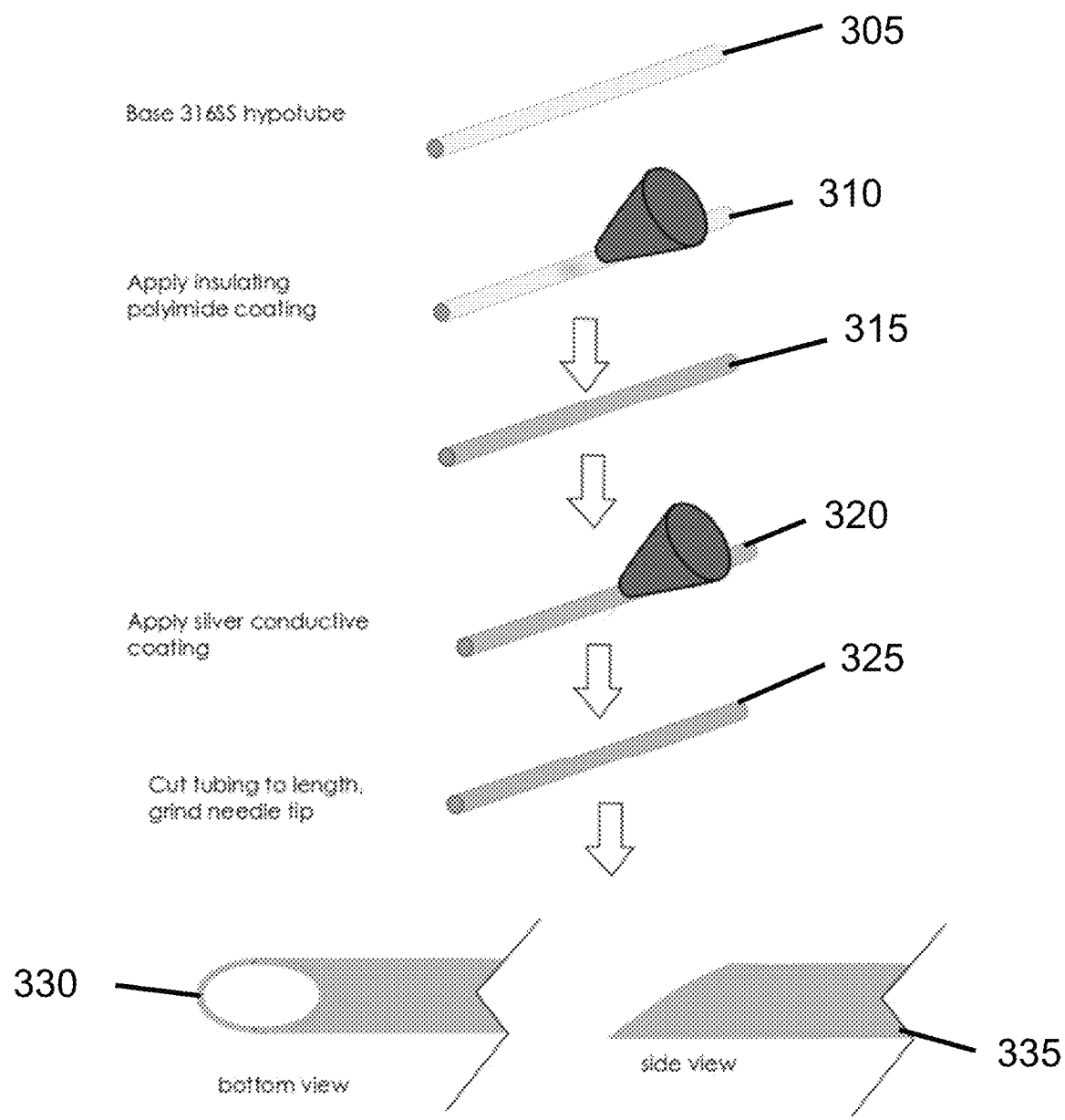
FIG. 3 is an exemplary diagram of various exemplary steps/procedures of a method for applying layers to the exemplary insertion device/apparatus according to an exemplary embodiment of the present disclosure.

FIG. 3 shows an exemplary diagram of a method 300 for applying layers to the exemplary insertion device/apparatus according to an exemplary embodiment of the present disclosure. As shown in FIG. 3, the multi-layer structure of the insertion device/apparatus can be produced by applying the layers with a spray process using, for example, an insulating and a conductive ink. For example, at procedure 305, a base hypotube can have an insulating polyimide coating applied thereto at procedures 310 and 315. At procedure 320, a silver conductive coating can be applied to the tube, and at procedure 325, the tube can be cut to length, and the tip of the insertion device/apparatus can be created by, e.g., grinding or laser cutting. Element 330 illustrates a bottom view of the finished insertion device/apparatus (e.g., needle, cannula, endoscope, laparoscope, etc.), and element 335 shows a side view of the finished insertion device/apparatus.

The exemplary procedure shown in FIG. 3 can limit the coatings to the outside of the tubing/needle leaving the center open. For example, eliminating masking and etching can keep the process for applying the layers relatively simple. After each procedure, the structure can be heated to remove any solvent, and to polymerize the coating.

Figure 4A:
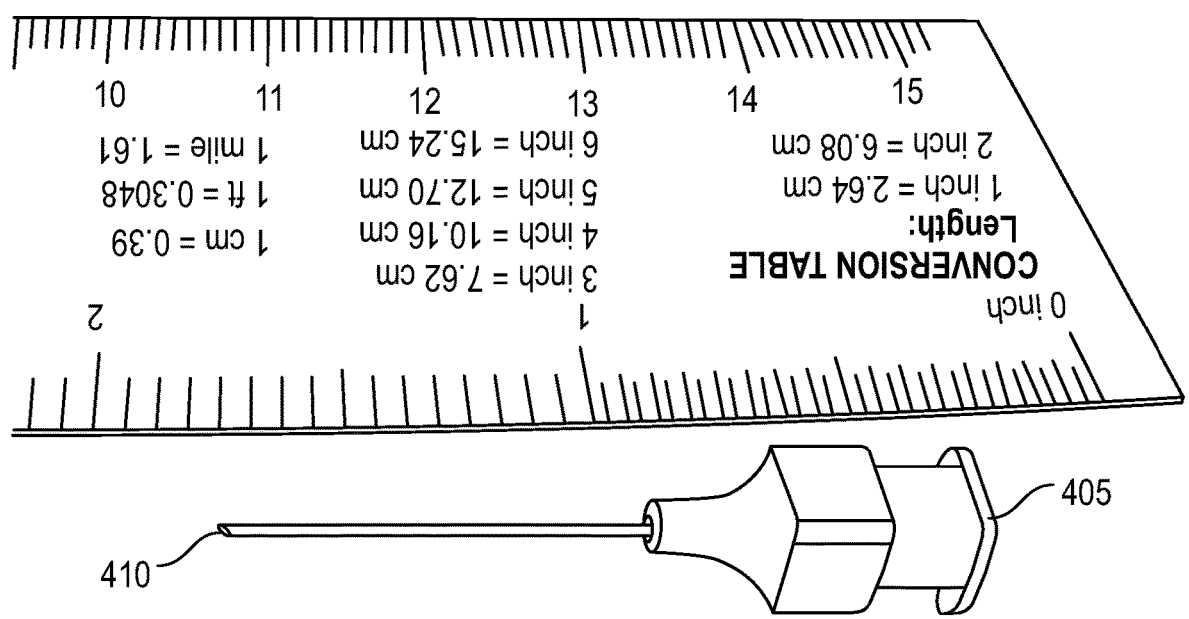
FIG. 4A is an exemplary image of the exemplary insertion device/apparatus according to an exemplary embodiment of the present disclosure.

FIG. 4A shows an exemplary image of exemplary needle 405 according to an exemplary embodiment of the present disclosure. For example, exemplary needle 405 was produced from 26 Ga 316SS tubing using the exemplary method shown in FIG. 3. The conductive coating on needle 405 was produced using a conductive silver ink (e.g., Creative Materials 118-43T). The base insulating coating is a polyimide (e.g., Jaro 650). As shown in FIG. 4A, needle tip 410 was laser cut. It should be understood that the tip of needle 450 can also be fabricated using other suitable techniques used to produce exemplary needles according to the exemplary embodiment of the present disclosure, such as, for example, grinding.

Figure 4B:
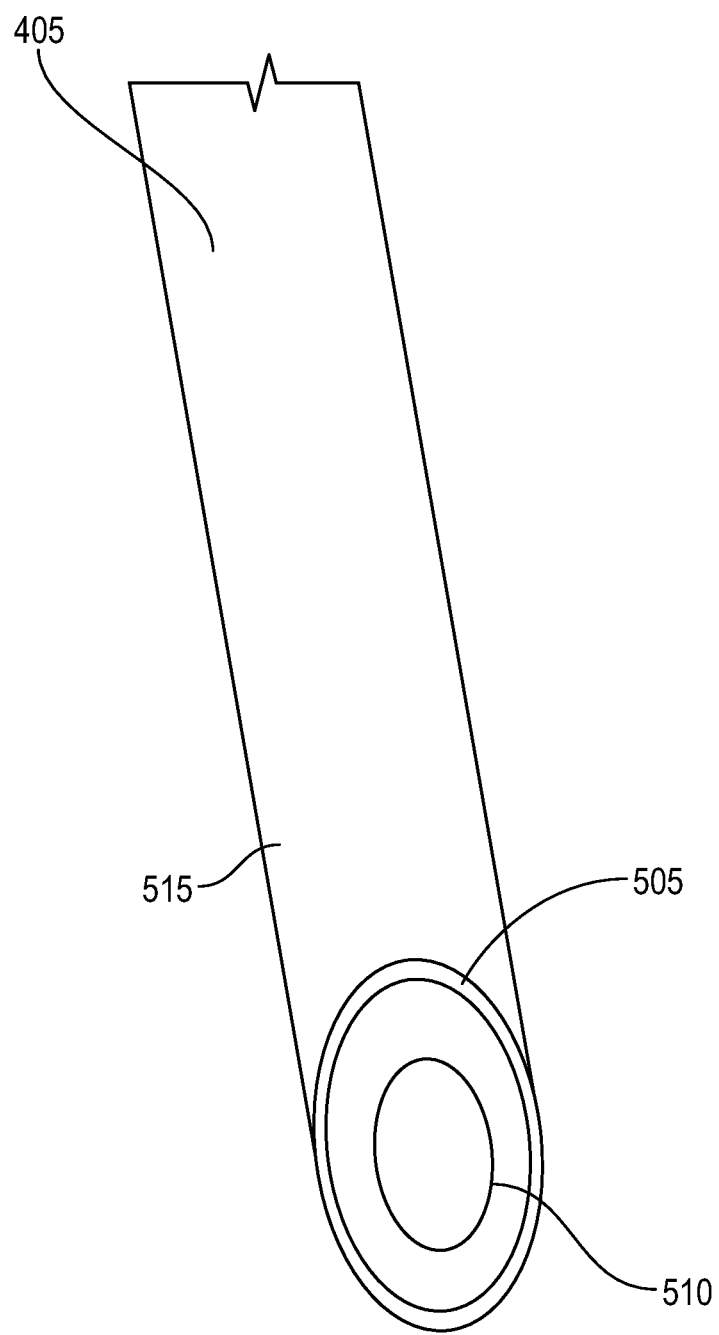
FIG. 4B is an exemplary close-up image illustrating the structure of the exemplary insertion device/apparatus fabricated with a layer of polyimide and an outer layer of silver conductive ink applied using a spray process according to an exemplary embodiment of the present disclosure.

FIG. 4B shows an exemplary close-up image illustrating the structure of the exemplary needle fabricated with a layer of polyimide (e.g., insulating layer 505 surrounding a stainless steel body 510) and an outer layer 515 composed of a silver conductive ink. Both insulating layer 505 and outer layer 515 were applied using an exemplary spray process (e.g., as described above in FIG. 3).

Figure 5:
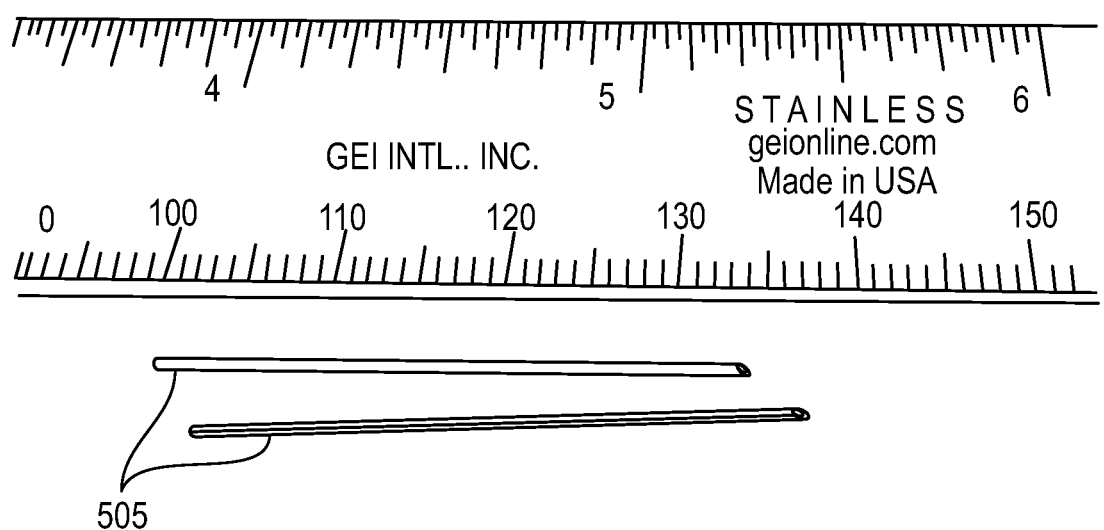
FIG. 5 is an exemplary image of exemplary insertion devices/apparatuses produced using a grinding process according to an exemplary embodiment of the present disclosure.

FIG. 5 shows an exemplary image of exemplary needles 505 produced using a grinding process according to an exemplary embodiment of the present disclosure. The layers of exemplary needles 505 can be produced through procedures other than spray coating such as electrochemical deposition, vapor deposition or sputtering, although not limited thereto. Masking can also be used to produce geometric patterns during the coating process. Alternatively or in addition, a mask can be applied after the coating, similar to the exemplary process used to produce printed circuit boards. In such an example, the mask can be spared during chemical etching.

Figure 6:
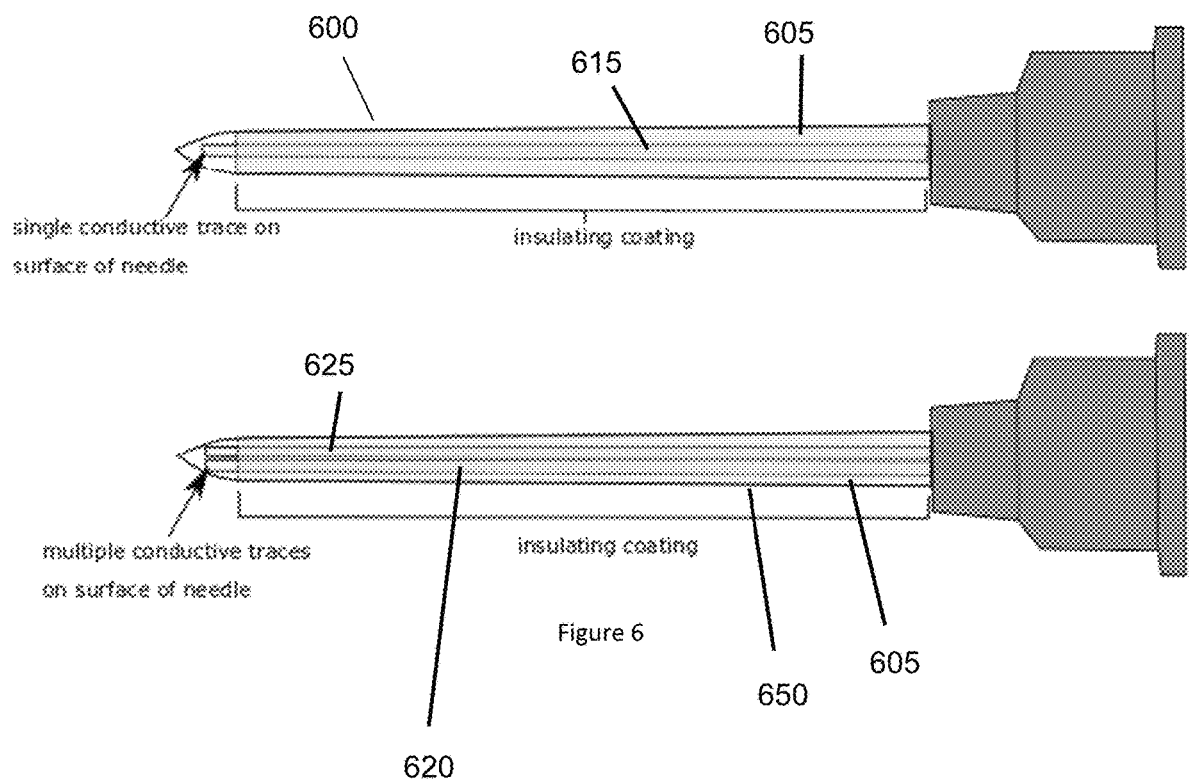
FIG. 6 is a set of side views of exemplary diagrams of different conductive traces used for the exemplary insertion device/apparatus according to an exemplary embodiment of the present disclosure.

FIG. 6 shows a set of side cross-sectional view and exemplary diagrams of needles 600 having different conductive traces according to an exemplary embodiment of the present disclosure. For example, as illustrated in FIG. 6, needle 600 can include an insulating coating 605, which can be used to insulate a single conductive trace 615 located on the surface of needle 600. Another needle 650 can also include an insulating coating 605. Further, needle 650 can include multiple conductive traces (e.g., traces 620, 625) on the surface of needle 650.

In conjunction with the exemplary embodiment shown in FIG. 6, the electrodes can be fabricated on the surface of a needle using procedures such as pad printing or screen printing with an outer insulating layer applied after. The insulating coating can be printed, deposited, or applied in the form of shrink tubing.

Figure 7:
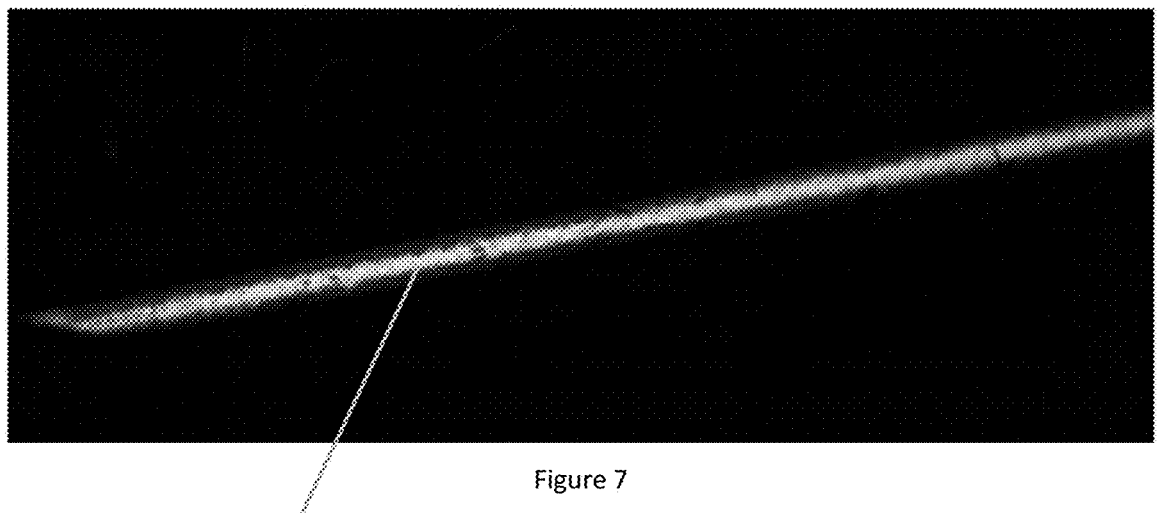
FIG. 7 is an exemplary image of an exemplary insertion device/apparatus having a surface electrode that was pad printed using ink according to an exemplary embodiment of the present disclosure.

FIG. 7 shows an exemplary image of an exemplary needle 705 having a surface electrode that was pad printed using ink according to an exemplary embodiment of the present disclosure. Exemplary needle 705 is a conventional 26 Ga hypodermic needle. The conductive surface electrode was pad printed using an ink specifically formulated for pad printing (e.g., Creative Materials 118-43T).

Figure 8:
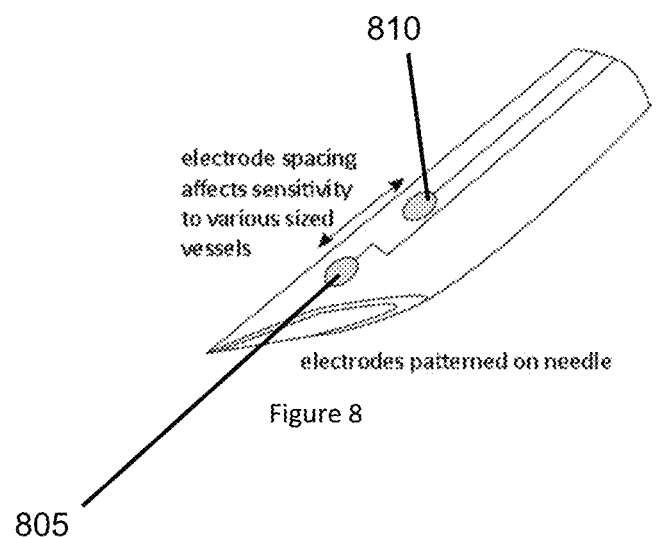
FIG. 8 is an exemplary expanded diagram of the distal end of the exemplary insertion device/apparatus having electrodes patterned on the exemplary insertion device/apparatus according to an exemplary embodiment of the present disclosure.

FIG. 8 shows an exemplary close-up diagram of the distal end of the exemplary insertion device/apparatus (e.g., needle) having electrodes 805, 810 patterned on the insertion device/apparatus according to an exemplary embodiment of the present disclosure. The spacing between electrodes 805, 810 can be varied to produce a physical filter to tailor sensitivity to different size structures. For example, the electrodes can be separated such that the spacing can be greater than the size of a specific artery. In such exemplary case, the electrodes should not be both be inside a blood vessel (e.g., an artery, a vein, etc.) at the same time which can affect electrical impedance.

Figure 9:
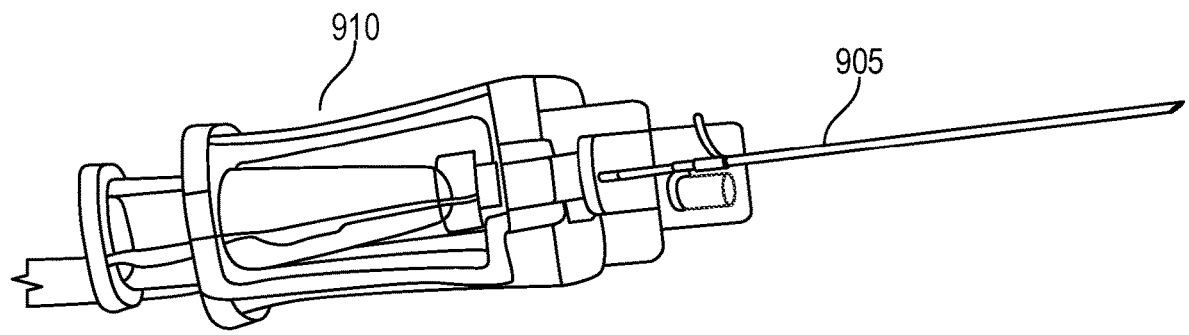
FIG. 9 is an exemplary illustration of the exemplary insertion device/apparatus according to an exemplary embodiment of the present disclosure.
Figure 10A:
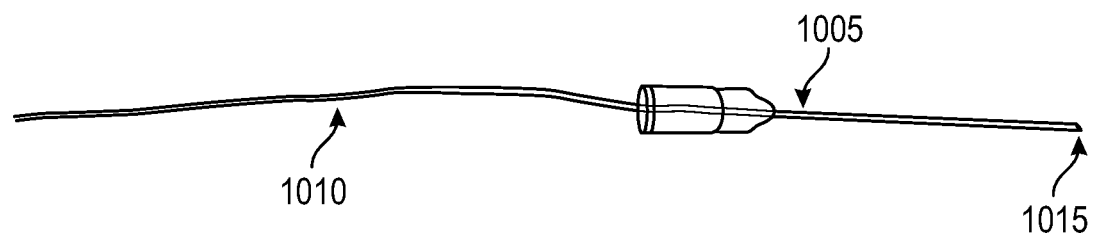
FIG. 10A is an exemplary image of the exemplary insertion device/apparatus having magnetic wires attached thereto according to an exemplary embodiment of the present disclosure.
Figure 10B:
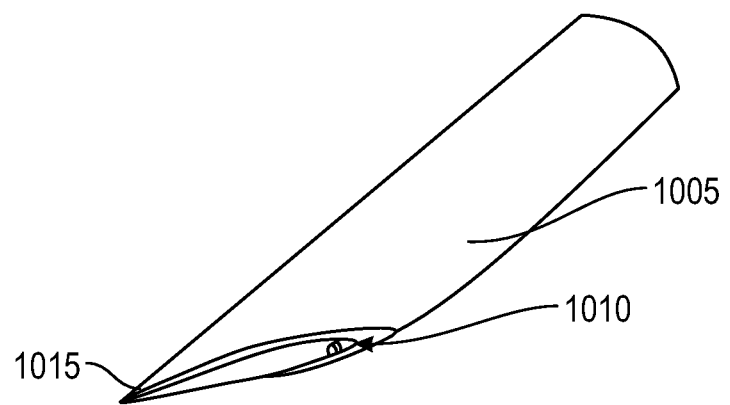
FIG. 10B is an exemplary diagram of the exemplary insertion device/apparatus shown in FIG. 10A illustrating the attachment of the magnetic wire according to an exemplary embodiment of the present disclosure.

FIG. 9 shows an exemplary image of the exemplary needle 905 according to another exemplary embodiment of the present disclosure. Electrodes connected to needle 905 can also be electrically connected to an external instrument using wires or a flex circuit. The flex circuit can form a flex cable for connection to the instrument. A clip (e.g., clip 910) can be used to provide an electrical connection to the needle 905, as well as contacting the needle body as well as the outer conductive coating.

Figure 11:
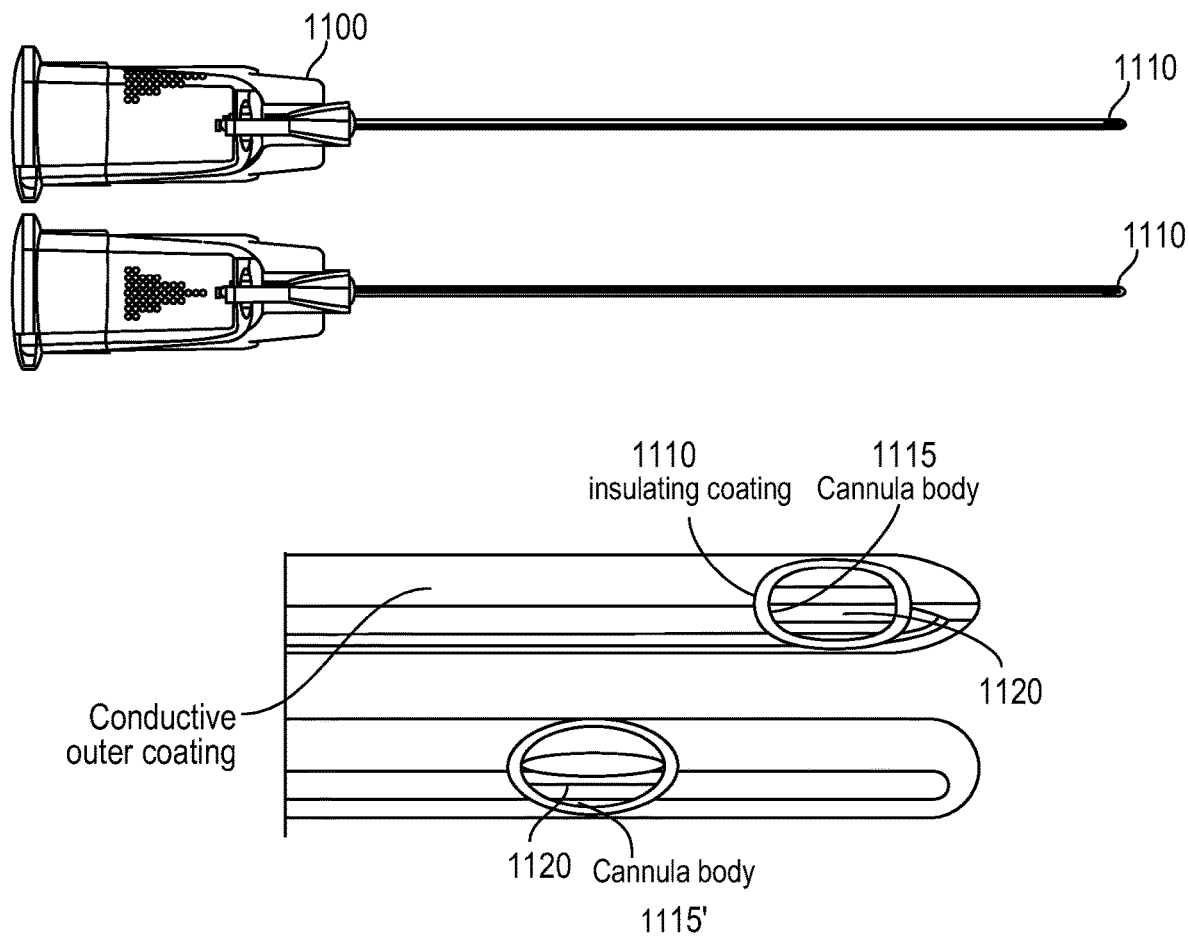
FIG. 11 is a set of side cross-sectional views of another exemplary embodiment of the exemplary insertion apparatus which provides an exemplary sensing technology implemented in the form of a cannula, according to yet another exemplary embodiment of the present disclosure.

FIG. 11 shows a set of side cross-sectional views of another exemplary embodiment of the exemplary insertion apparatus 1100 which provides an exemplary sensing technology implemented in the form of a cannula, according to yet another exemplary embodiment of the present disclosure. As illustrated in FIG. 11, a cannula body 1115, 1115' of an injection cannula 1100 can be coated (e.g., with an insulating coating 1120) to produce a sensing structure around the cannula openings 1120, 1120'.

Figure 13:
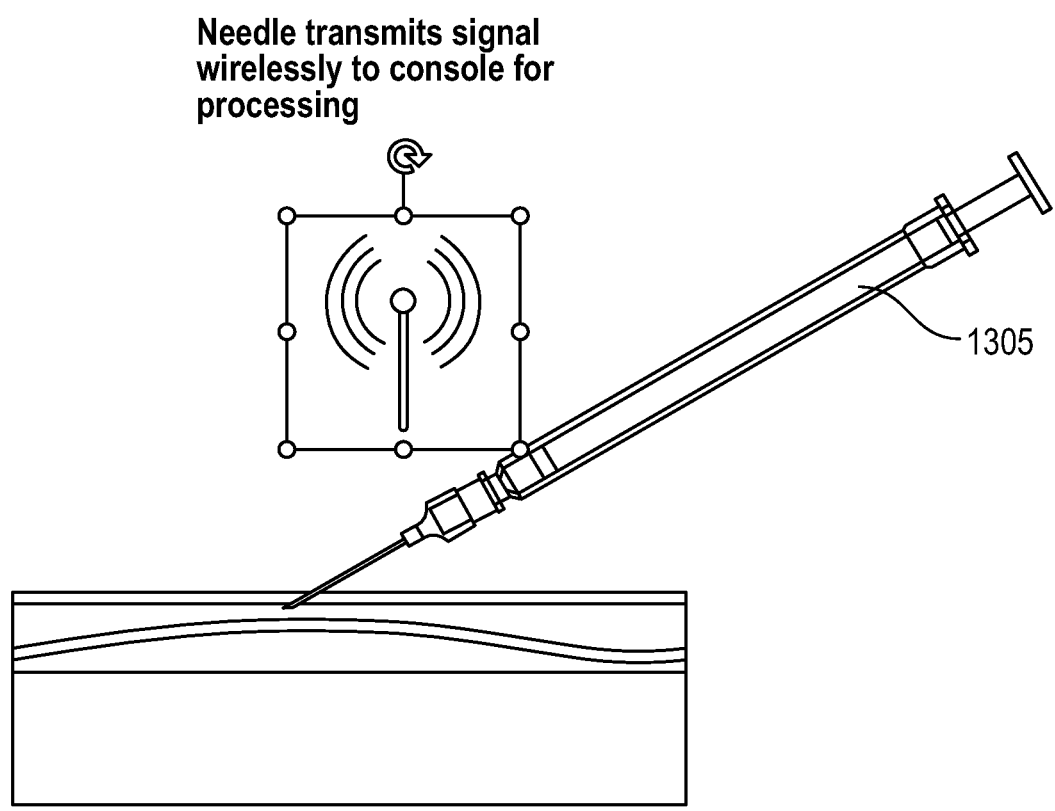
FIG. 13 is an exemplary diagram illustrating wireless transmission of information from the exemplary insertion device/apparatus for use in determining the tissue type according to an exemplary embodiment of the present disclosure.

FIG. 13 shows an exemplary diagram illustrating that information can be wirelessly transmitted from a transmitted of the exemplary insertion (e.g., needle) apparatus 1305 for use in determining the tissue type according to an exemplary embodiment of the present disclosure. For example, an exemplary processor, microprocessor, etc. can be embedded in either at any portion of the needle apparatus 1305, including but not limited in the needle itself, which can be used to collect the electrical information obtained using the electrodes. This information can be sent to another device (e.g., using a wired or wireless transmission medium, as discussed below), which can be used to analyze the information, determine the impedance, and ascertain the tissue type.

Figure 14:
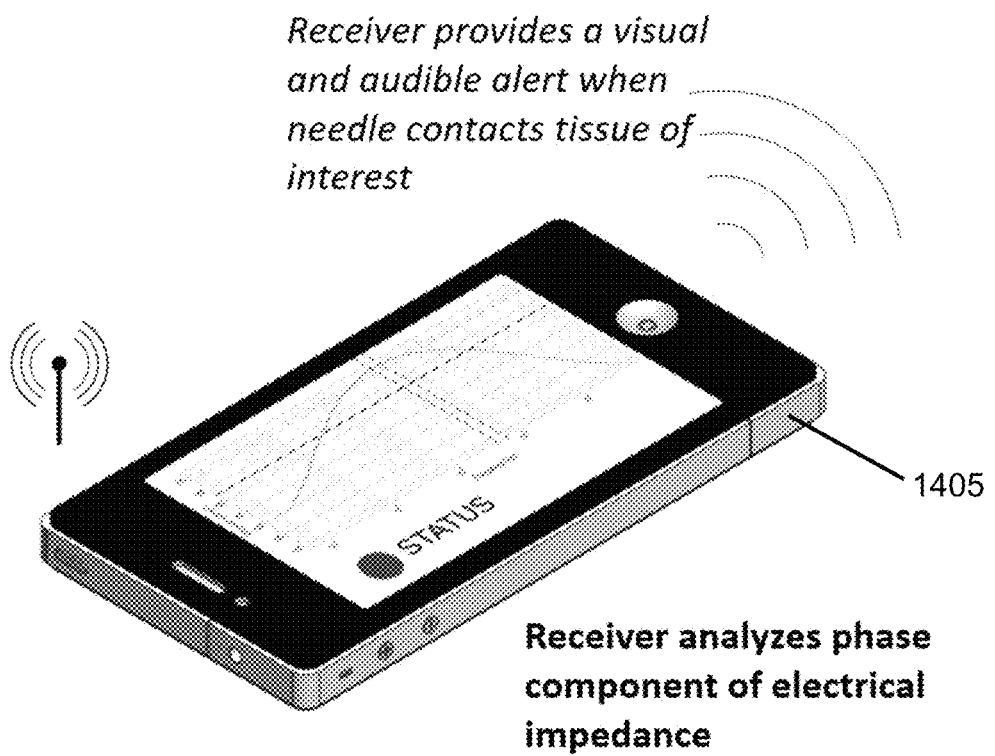
FIG. 14 is an exemplary diagram of an exemplary mobile device used to receive the wireless transmission of information from the exemplary insertion device/apparatus shown in FIG. 13, which can be used to determine the tissue type according to an exemplary embodiment of the present disclosure.

FIG. 14 shows an exemplary diagram of an exemplary mobile device 1405 used to receive the wireless transmission of information from the exemplary insertion (e.g., needle) apparatus illustrated in FIG. 13 to determine the tissue type according to an exemplary embodiment of the present disclosure. For example, exemplary needle apparatus 1305 can have a wireless communication chip embedded therein (including in any part thereof, such as the needle, etc.), which can be powered using an internal battery, through an external electrical connection, or through any suitable wireless power medium. The power supplied to needle apparatus 1305 can be used to power the wireless communication chip, as well as any microprocessor embedded in needle apparatus 1305. Alternatively, power can be obtained from electrical signals present in the body of the subject, which can provide sufficient power to send a burst signal of information from needle apparatus 1305 to device 1405.

The exemplary tissue detection system/apparatus can include a single insertion device/apparatus (e.g., a needle, a cannula, etc.). However, the exemplary tissue detection system/apparatus can include a plurality of insertion devices (e.g., an array of needles, an array of cannulas, an array of mixture of needle(s)/cannula(s), etc.). Each insertion device in the array thereof can be of the same electrode design/structure (e.g., one design of the various exemplary electrode designs/structures described above). However, each insertion device in the array can have a different design/structure, or a subset of the insertion devices can have one design/structure while another subset can have a different design/structure. Each insertion device in the exemplary array thereof can perform tissue detection as described above, and each insertion device can also perform a medical function (e.g., the administering of a material or a substance or the removal of a biopsy sample and/or other fluid, tissue, cells or material). Thus, one or more insertion devices in the exemplary array thereof can perform the tissue detection, while one or more other needles can perform the medically-related functions. The exemplary array of the insertion devices can also be used to increase the accuracy of the tissue detection by increasing the number of the electrodes that are used to determine the impedance. Additionally, a comparison of the impedance between the insertion devices in the array can also be used to determine the tissue type.

Exemplary Operation and Determination of Tissue Type

The exemplary insertion device/apparatus can be used to measure impedance around the tip of the needle. Impedance, Z can be a measure of the opposition of a medium to alternating current flow at a given frequency. Z can be defined by, for example:

$$Z = R + jXc$$

where R can be resistance and Xc can be reactance. Resistance can vary with geometry and resistivity of the medium. Reactance can vary with frequency and capacitance.

As the exemplary insertion device/apparatus passes through the different tissues, the instrument can read the impedance and phase angle at the needle tip at a fixed frequency, for example, 10,000 Hz. As the exemplary insertion device/apparatus passes through different types of tissue, the measured/inferred impedance can show a distinct change. Electronics integrated into the hub of the exemplary insertion device/apparatus can provide a measurement of the current. The exemplary apparatus can be used to provide either a warning (e.g., to avoid a procedure) or a helpful alert (e.g., to proceed with a procedure).

The exemplary insertion devices/apparatuses can be used as a replacement for current disposable hypodermic needles. Potential uses can include injection and minimally invasive instrument introduction. During an injection procedure, for example a filler injection, the clinician can insert the exemplary insertion devices and manipulate the needle as per normal operation. For example, as the exemplary insertion device/apparatus penetrates a blood vessel (e.g., an artery, a vein, etc.), the exemplary apparatus can provide an audible and/or a visual alert to warn the clinician that it may be hazardous to inject a particular material (e.g., the filler). For other types of injections, for example, an intradermal vaccine injection, a clinician can be provided with an indication that the needle is in the intradermal space in which case, the clinician can wait for an alert before injecting.

Electrical connections can be made to connect the electrodes to the electronics that can sense and interpret the electrical impedance. The electronics can be integrated into the needle, as close as possible to the electrodes. Exemplary electronics can include a source to generate an oscillating voltage and a measurement device to determine the magnitude and phase between the applied voltage and the current. The electronics can be packaged to be integrated into the hub of the exemplary insertion device/apparatus which can typically be used to connect the exemplary insertion device/apparatus to a syringe. For example, Analog Devices manufactures a single chip in an 8 mm×8 mm package, the ADuCM350, which can be used to analyze impedance over a wide range of frequencies. Such exemplary chip can easily fit within the envelope of a standard Luer hub. The connection between the electrodes and the integrated electronics can be made using traces produced at the same time as the electrodes. The ADuCM350 chip can contain an audio driver which can be used to produce an audible sound to alert a user when the exemplary insertion device/apparatus has been inserted into and/or penetrated a specific tissue structure.

The exemplary electronics can communicate wirelessly with an external receiver for further processing. Wireless communication can be performed using any low power hardware, for example Bluetooth LE, ANT, RF, or Zigbee. The exemplary apparatus can be tailored to focus on the response at a very narrow band of frequencies rather than across a broad spectrum. Therefore, custom electronics tailored for a specific tissue type can be much simpler than a general analyzer. The exemplary insertion device/apparatus can be further simplified by offloading processing to an external console. The electronics on the exemplary insertion device/apparatus can be limited to simply measuring the current in response to the input, transmitting the response to the console via a low power RF or other transmission scheme.

Exemplary Additional Discussion

As discussed herein, the exemplary insertion device/apparatus can be used in various injection procedures which require injection into specific tissues such as fat, septae, or the intradermal space. The exemplary insertion device/apparatus can also be used in cardiac catheterization (e.g., trocars), which can be used to introduce catheters into a blood vessel (e.g., an artery, a vein, etc.). The exemplary insertion device/apparatus can be used in various other applications including, but not limited to, anesthesia procedures, as well as during ablation procedures to determine when the ablation electrodes are within a specific tissue type. The exemplary insertion device/apparatus can be integrated into a catheter to be used inside the body. For example, the insertion device/apparatus can be used as part of a transseptal needle, which can be used during minimally invasive cardiac procedures. Any suitable fabrication procedure/technique can be used to produce printed circuit boards can be used to produce the exemplary insertion device/apparatus structure. Exemplary electrodes can be rigid or flexible.

Figure 19A:
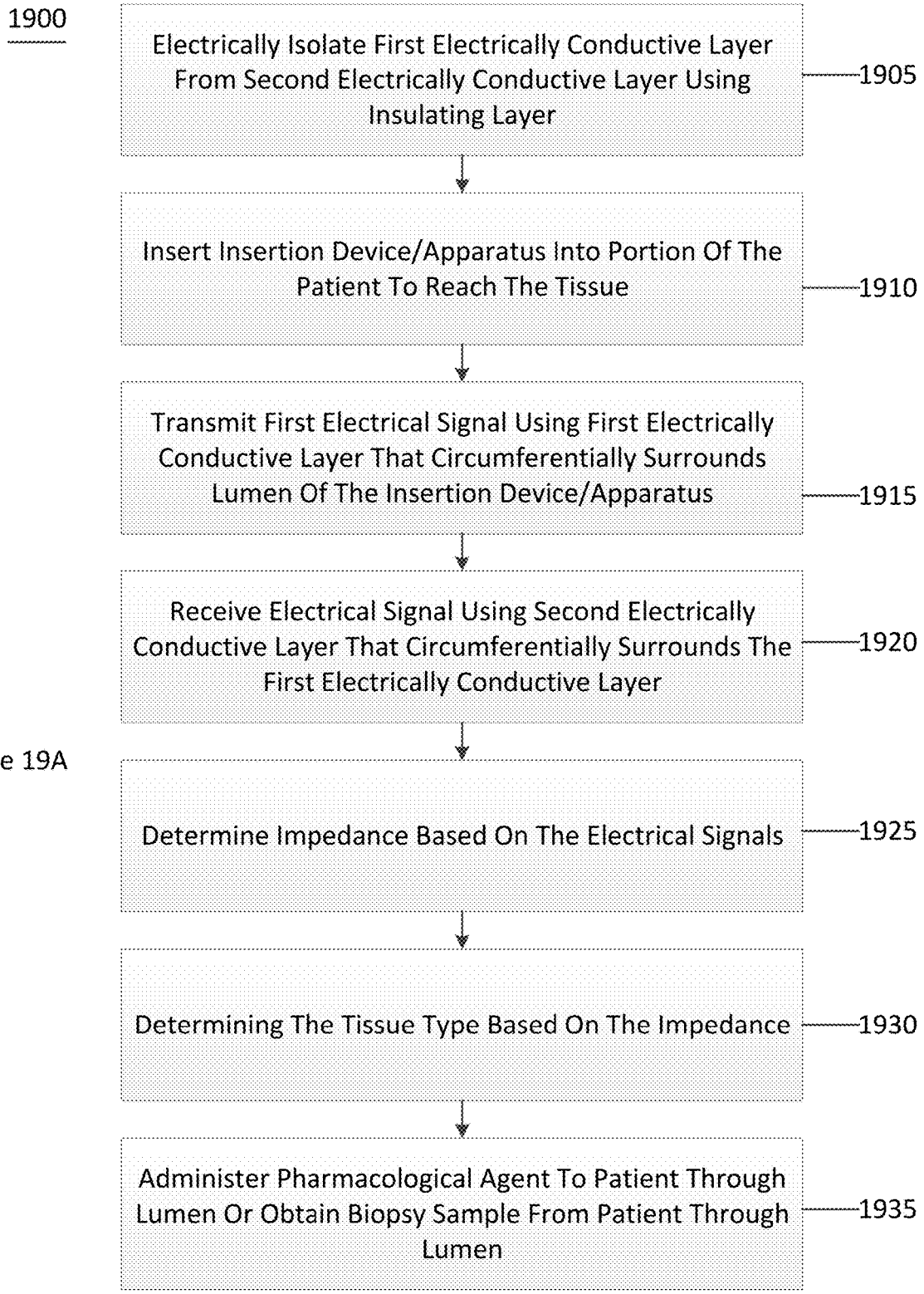
FIGS. 19A-19C are exemplary flow diagrams of exemplary methods of determining a type of a tissue of a subject using the exemplary insertion device/apparatus.
Figure 19B:
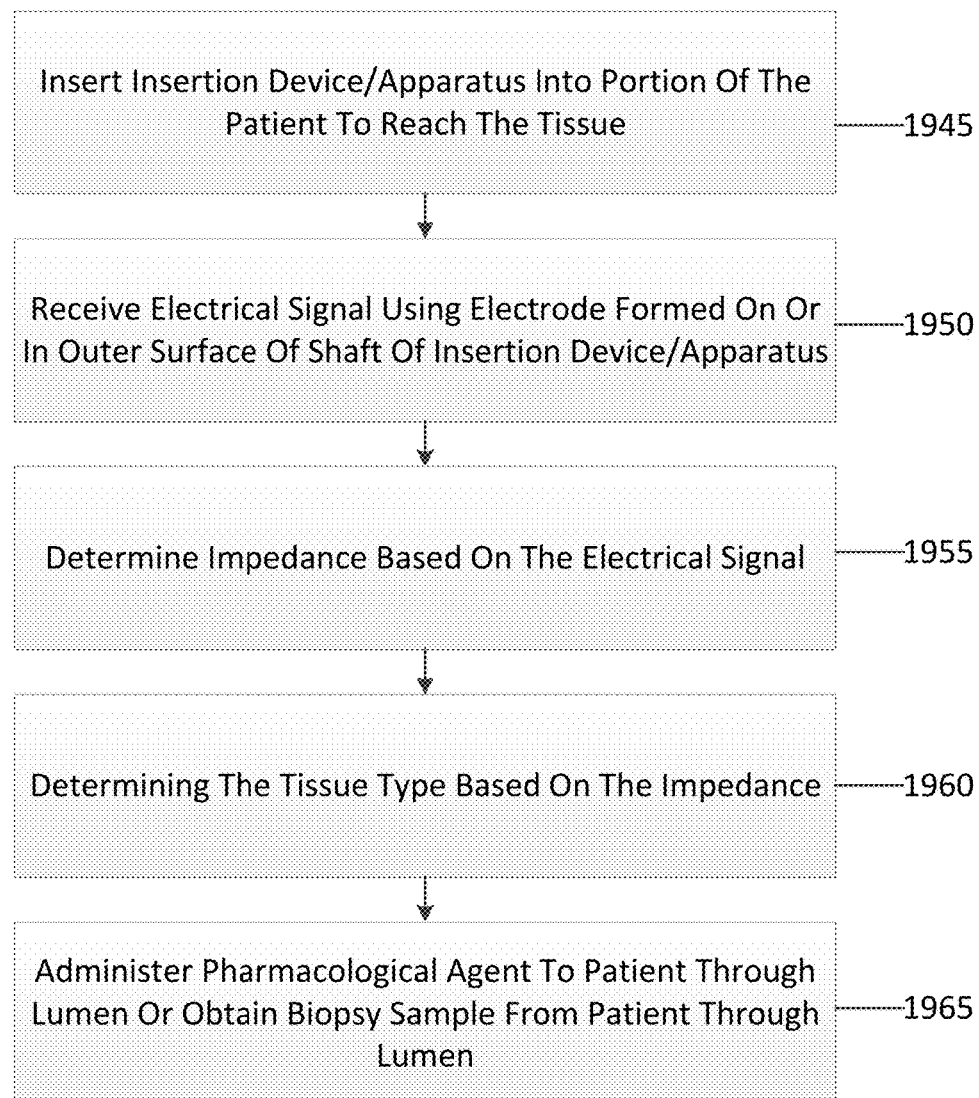
Figure 19C:
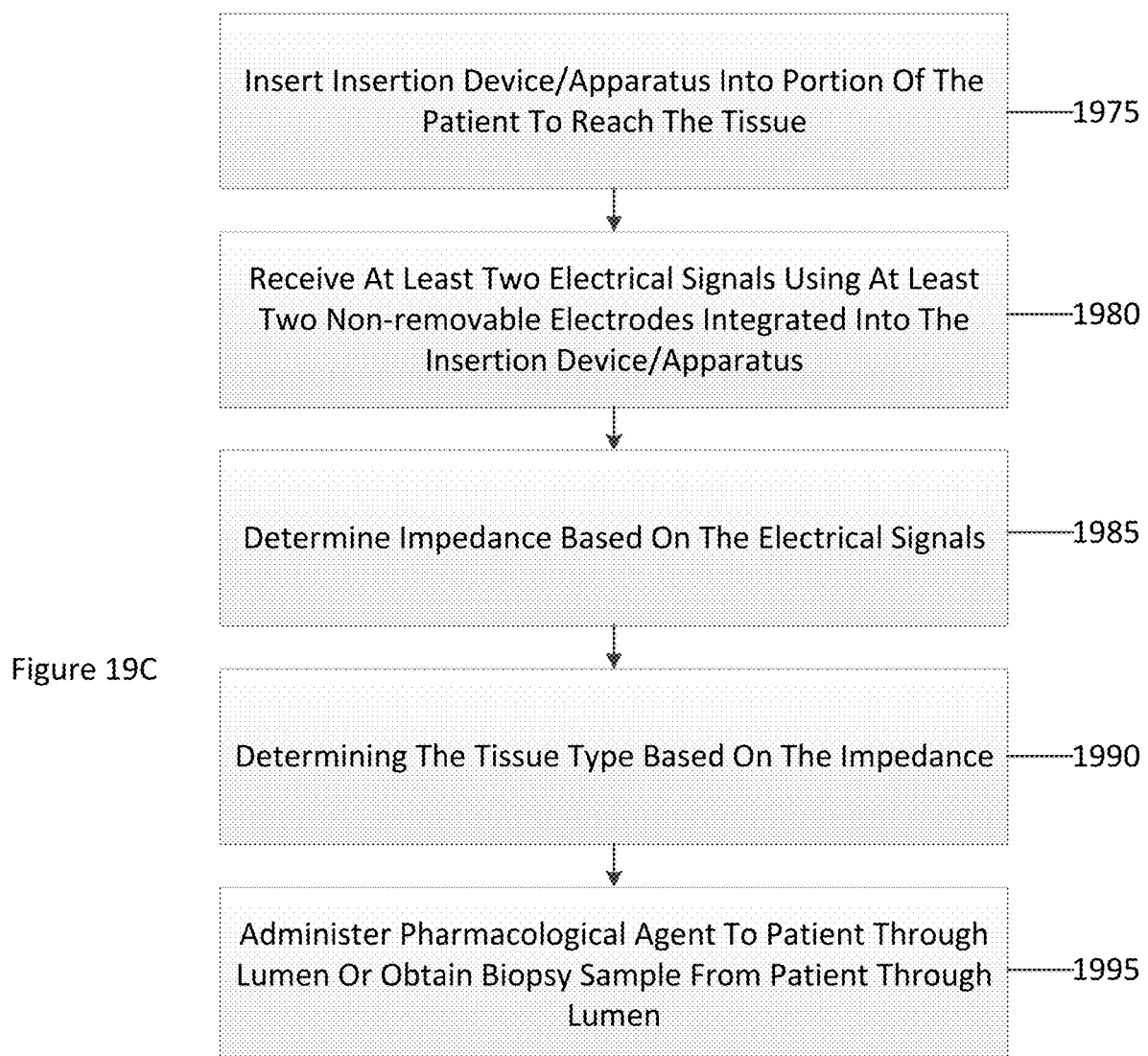

FIGS. 19A-19C are exemplary flow diagrams of exemplary methods 1900, 1940, and 1970 for determining a type of a tissue of a subject using the exemplary insertion device/apparatus. For example, as shown in FIG. 19A, at procedure 1905, a first electrically conductive layer in the insertion device/apparatus can be electrically isolated from a second electrically conductive layer in the insertion device/apparatus using an insulating layer. At procedure 1910, the insertion device/apparatus can be inserted into the portion of the subject to reach the tissue. At procedure 1915, a first electrical signal can be transmitted and/or received using the first electrical conductive layer, which circumferentially surrounds a lumen of the insertion device/apparatus. In one exemplary embodiment of the present disclosure, the AC wave form that was generated can pass through analog conditioner circuitry to the electrode(s). Impedance measurement of tissue between electrodes can impact the wave form which can then be measured using exemplary digital processing techniques (e.g., synchronous detection, 4 fs, etc.) At procedure 1920, the electrical signal (or another electrical signal) can be received from the second electrically conductive layer, which circumferentially surrounds the first electrically conductive layer. At procedure 1925, an impedance can be determined based on the ratio of the transmitted and received electrical signals. At procedure 1930, the tissue type can be determined based on the impedance. In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1935, any material and/or substance (e.g., a pharmacological agent, drug, filler, therapeutics, biologics, cellular materials, stem cells, genetic materials, immunotherapy agents, etc.) can be administered to the subject through the lumen or a biopsy sample and/or other fluid, tissue, cells or material can be obtained from the subject through the lumen.

As shown in the flow diagram of FIG. 19B, at procedure 1945, the insertion device/apparatus can be inserted into the portion of the subject to reach the tissue. At procedure 1950, an electrical signal can be transmitted and/or received using an electrode formed on or in an outer surface of the shaft of the insertion device/apparatus. At procedure 1955, an impedance can be determined based on the electrical signal. At procedure 1960, the tissue type can be determined based on the impedance. Either the magnitude and/or phase components of the impedance can be used to distinguish the tissue type by comparing the measured values with known values (e.g., at one frequency or a narrow band of frequencies). In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1965, any material and/or substance (e.g., a pharmacological agent, drug, filler, therapeutics, biologics, cellular materials, stem cells, genetic materials, immunotherapy agents, etc.) can be administered to the subject through the lumen or a biopsy sample and/or other fluid, tissue, cells or material can be obtained from the subject through the lumen.

As shown in the flow diagram of FIG. 19C, at procedure 1975, the insertion device/apparatus can be inserted into the portion of the subject to reach the tissue. At procedure 1980, at least two electrical signals can be received using at least two non-removable electrodes integrated into the insertion device/apparatus. In one exemplary embodiment of the present disclosure, the AC wave form that was generated can pass through analog conditioner circuitry to the electrodes. Impedance measurement of tissue between electrodes can impact the wave form which can then be measured using exemplary digital processing techniques (e.g., synchronous detection, 4 fs, etc.) At procedure 1985, an impedance can be determined based on the at least two electrical signals. At procedure 1990, the tissue type can be determined based on the impedance. In one exemplary embodiment, feedback may be given to the user by providing appropriate information to the user to an optical display, auditory device or a haptic device. Additionally or alternatively, a tactile response can be provided on the insertion device and/or on the endoscope holding such insertion device. At procedure 1995, any material and/or substance (e.g., a pharmacological agent, drug, fluid (e.g. blood, plasma, and other fluids typically administered through a needle), filler, therapeutic agents, cellular materials, stem cells, cells (e.g. adipocytes, lymphocytes, etc.), tissues (e.g. adipose tissue, bone marrow, etc.), genetic materials, immunotherapy agents, etc.) can be administered to the subject through the lumen or a material, tissue, cells, fluid and/or a biopsy sample can be obtained from the subject through the lumen.

Figure 20A:
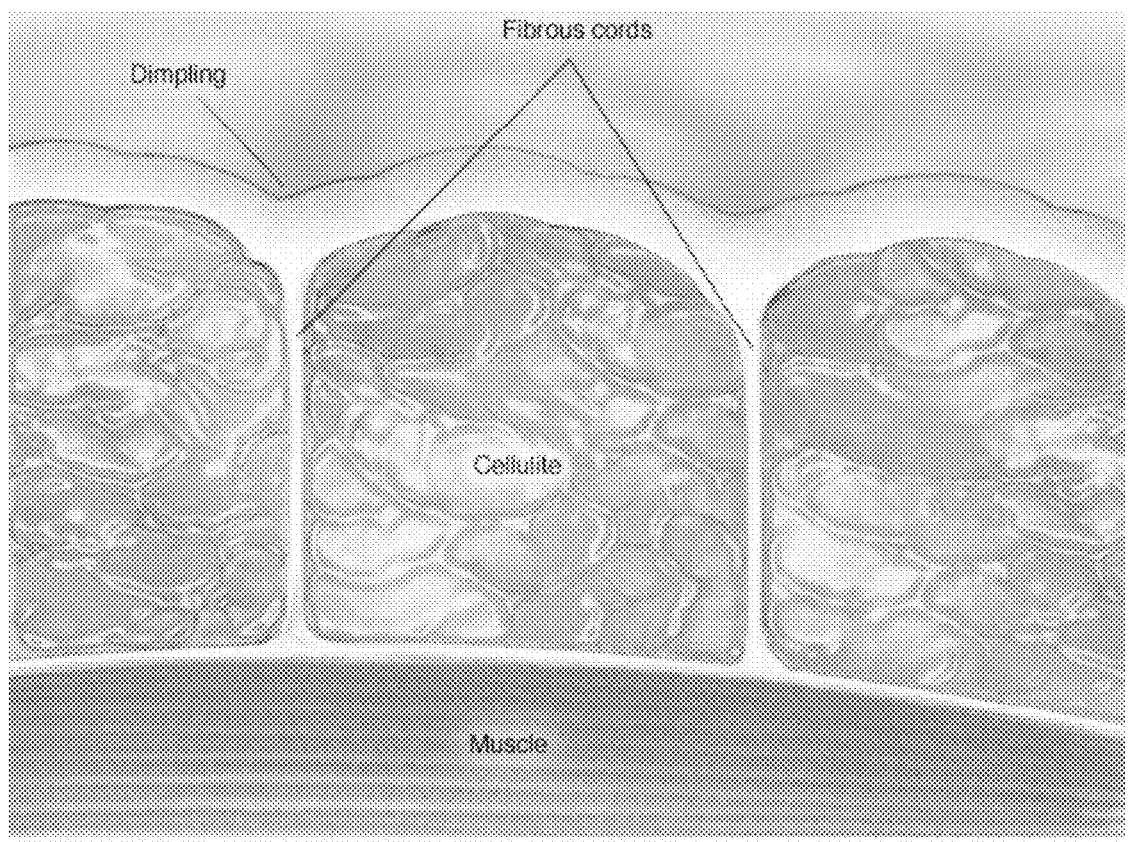
FIGS. 20A and 20B are illustration of an exemplary treatment of edematous fibrosclerotic panniculopathy (EFP), commonly known as cellulite, through the injection of a particular substance in accordance with the exemplary embodiment of the present disclosure.
Figure 20B:
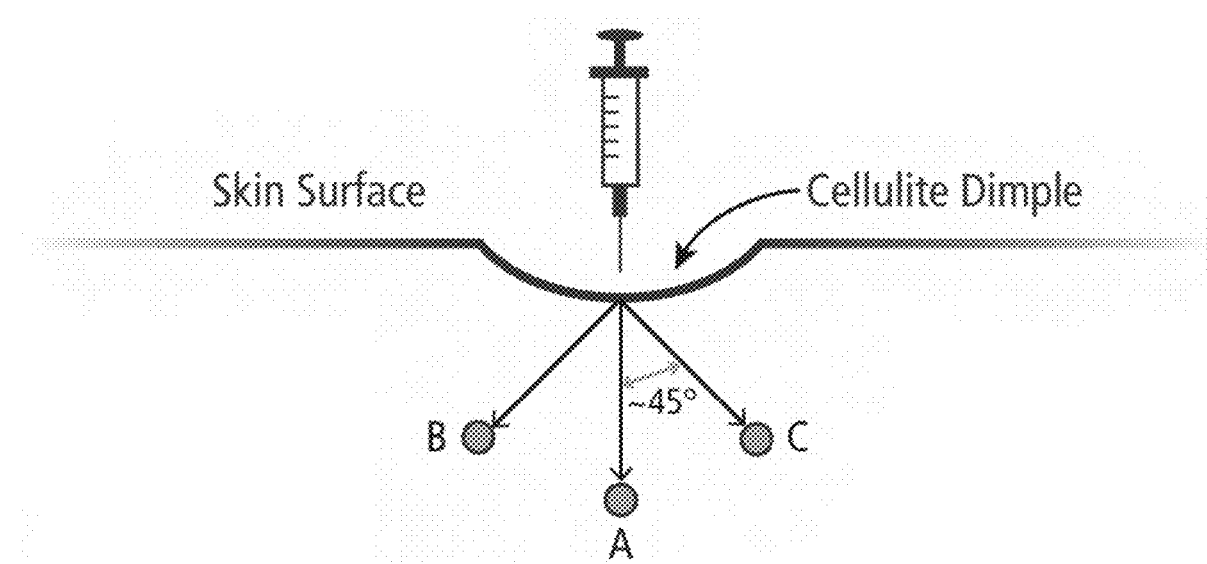

In accordance with various exemplary embodiments of the present disclosure, it is beneficial to utilize the exemplary insertion device/apparatus to perform other exemplary procedures which are significantly benefitted with the identification of the tissue into which certain materials and/or substances are being inserted and/or injected. FIG. 20A shows an exemplary illustration of the differ layers and sections within a tissue sample, and FIG. 20B provide and exemplary illustration of an application of the exemplary embodiments of the insertion devices/apparatuses according to the present disclosure which can be used the treatment of edematous fibrosclerotic panniculopathy (EFP), commonly known as cellulite, by an injection of an enzyme into the tissue, such as, e.g., collagenase. For example, the enzyme can be injected locally into the fat in order to break down the fibrous cords, also called septae which are responsible for causing the dimpled appearance of cellulite. The exemplary insertion device/apparatus according to the exemplary embodiments of the present disclosure incorporating and/or utilizing the exemplary impedance sensing as described herein can be used to provide an indication and/or direction of when the tip of the insertion device/apparatus is within the fat before the injection. This beneficially facilitates the enzyme to be injected close to the septae. The exemplary injection procedure is shown in FIG. 20B.

Figure 20C:
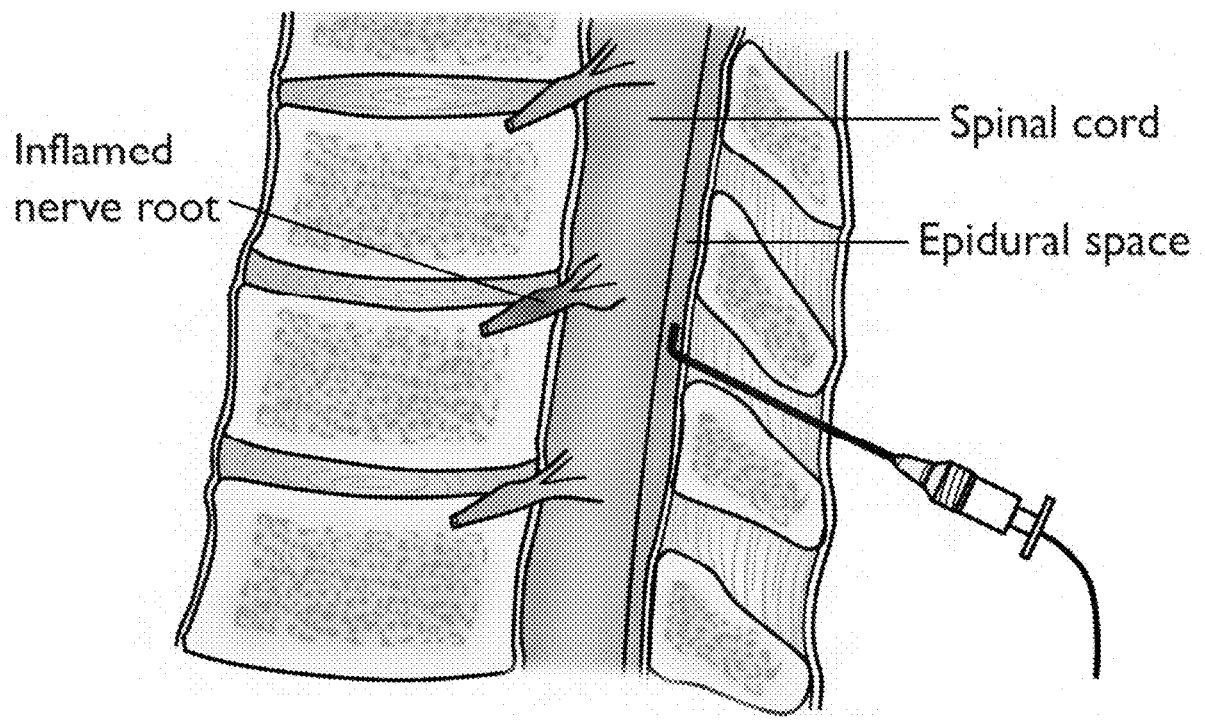
FIG. 20C is an illustration of an exemplary procedure involving a spinal injection performed to alleviate the source of pain or discomfort, in accordance with the exemplary embodiment of the present disclosure.

FIG. 20C illustrates an exemplary procedure involving a spinal injection which can be performed to diagnose the source of back, leg, neck, or arm pain (diagnostic) and also to relieve pain (therapeutic). The exemplary insertion devices/apparatus incorporating impedance sensing functionality and/or configurations can be used to provide a user with an indication of when the tip of such exemplary insertion devices/apparatus is within the epidural space. The exemplary insertion devices/apparatuses (and/or a system connected thereto) can be programmed or otherwise configured to detect the unique impedance signature and/or information indicative or representative of the epidural fluid. The exemplary insertion devices/apparatus also be used for an injection of various substances into the tissue, such as steroids into joints in the spine such as the sacroiliac joint, when the exemplary insertion devices/apparatus determines that a certain tissue type or an opening is reached.

Figure 20D:
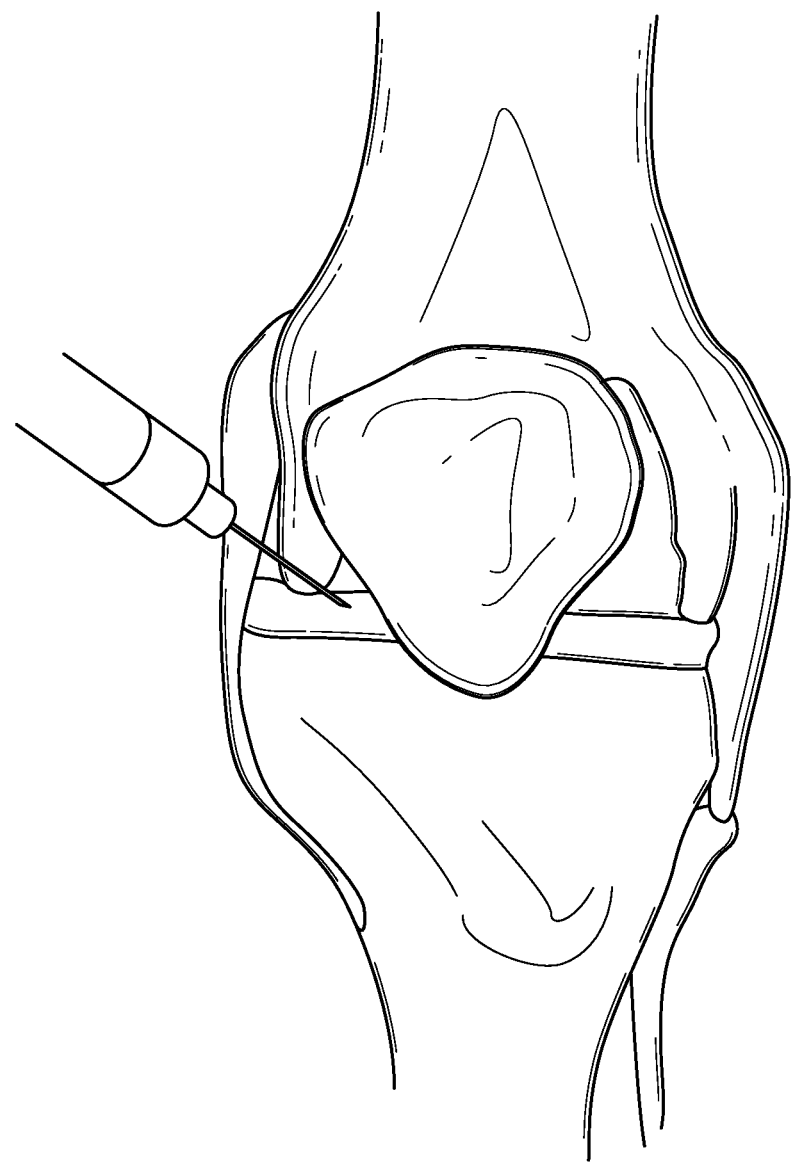
FIG. 20D is an illustration of an exemplary procedure involving an injection of substances (e.g., such as platelet rich plasma (PRP) or hyaluronic acid (HA)) into the synovial space in accordance with the exemplary embodiment of the present disclosure.

FIG. 20D shows an illustration of an exemplary procedure involving an injection of substances (such as, e.g., platelet rich plasma (PRP)) into cartilage of joins (e.g., knees, elbows, etc.), in accordance with the exemplary embodiment of the present disclosure. As illustrated in FIG. 20D, the exemplary insertion device/apparatus incorporating and/or utilizing the exemplary impedance sensing as described herein can provide an indication of when the tip of the exemplary insertion apparatus is within the cartilage. The exemplary insertion devices/apparatuses (and/or a system connected thereto) can be programmed or otherwise configured to detect the unique impedance signature and/or information indicative or representative of cartilage.

Further, for example, the exemplary insertion devices/apparatuses described herein can be utilized in various cellulite treatment applications based on the detection of the unique impedance signature and/or information of the tissue. Some of such exemplary applications are described in, e.g., U.S. Patent Publication No. 2018/0250217 and Michael P. Goldman et al., "Phase 2a, randomized, double-blind, placebo-controlled dose-ranging study of repeat doses of collagenase *Clostridium histolyticum* for the treatment of edematous fibrosclerotic panniculopathy (cellulite)", Poster Presented at the 73rd Annual Meeting of the American Academy of Dermatology, Mar. 20-24, 2015; San Francisco, Calif., the entire disclosures are incorporated herein by reference.

In a further exemplary embodiment of the present disclosure, the exemplary insertion device/apparatus can be configured to be used to extract or aspirate bodily fluids, cells or tissues from a body, including, e.g., a subject. In one example, a syringe and needle can be used as the insertion device/apparatus to extract or aspirate materials, fluids, solutions, compounds, etc. which are well-known in the medical, dental and veterinary fields in general. Indeed, such exemplary utilization of the insertion device/apparatus according to the exemplary embodiments of the present disclosure can facilitate a greater precision and safety for the subject. Non-limiting examples of use of the exemplary insertion device/apparatus can include phlebotomy procedures used to draw blood samples, spinal taps used to extract cerebrospinal fluid from the spinal column, joint taps used to extract synovial fluid, needle biopsies to aspirate a sample of cells or tissue and the aspiration of bone marrow samples for typing and transplantation.

One having ordinary skill in the art may readily understand, based on the review of the present disclosure, that such exemplary embodiment of the insertion device/apparatus may be used in the same or similar manner as other methods described in the present application in which materials, cells, compounds, agents, enzymes, fillers, fluids, etc. are inserted into a body at certain determined tissues types, and instead by extracting or aspirating the targeted fluid, materials, compounds, agents, enzymes, fillers, fluids, etc. This can be done, in one non-limiting example, by—instead of pushing the syringe plunger to expunge a fluid or other materials—pulling back on the syringe plunger to create suction or a vacuum that draws the targeted fluid, materials, cells, compounds, agents, enzymes, fillers, fluids, etc. into the syringe (e.g., in a reverse direction).

Figure 21A:
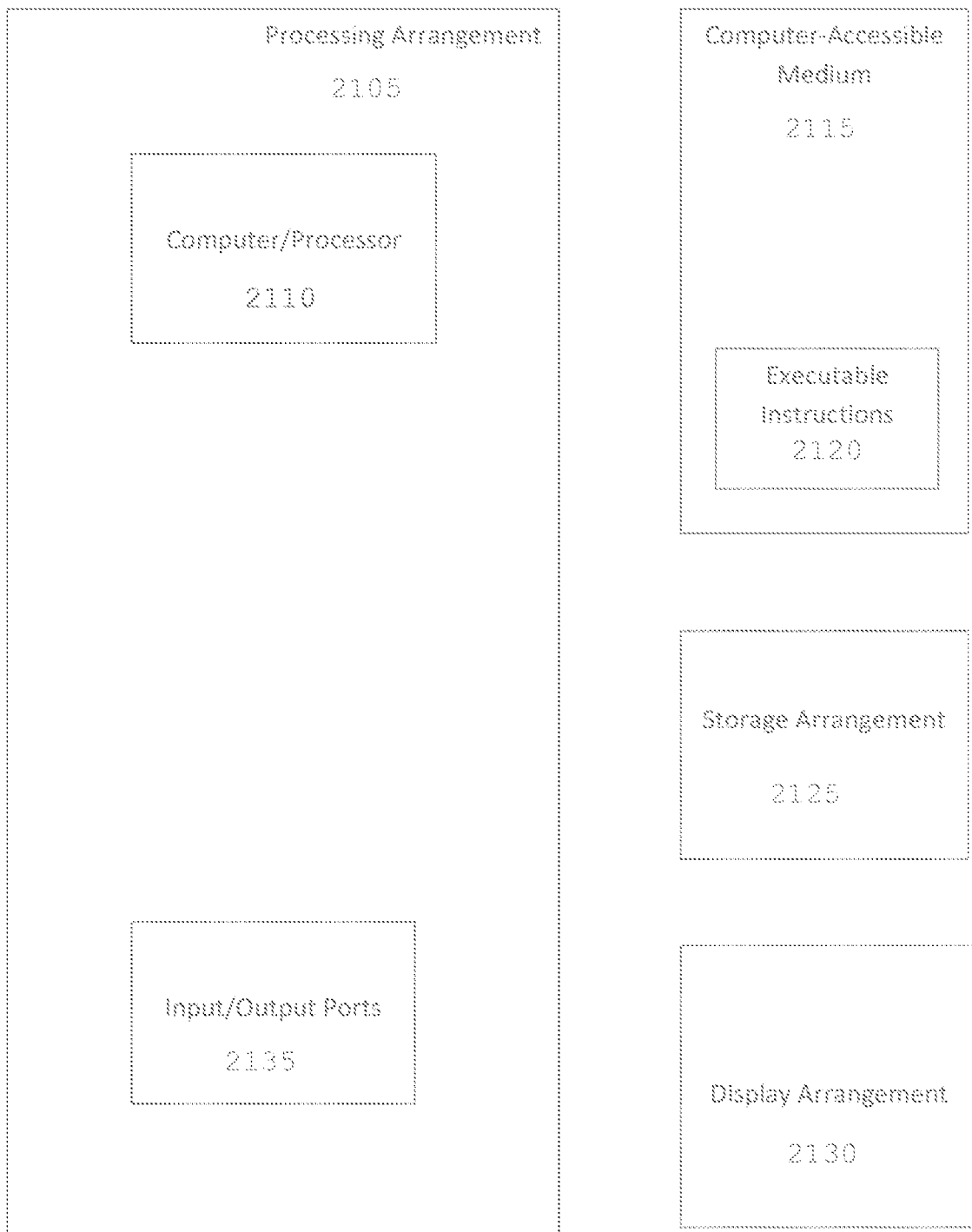
FIG. 21A is an illustration of an exemplary block diagram of an exemplary system in accordance with certain exemplary embodiments of the present disclosure.

FIG. 21A shows a block diagram of an exemplary embodiment of a system according to the present disclosure. For example, exemplary procedures in accordance with the present disclosure described herein can be performed by a processing arrangement and/or a computing arrangement 2102. Such processing/computing arrangement 2102 can be, for example entirely or a part of, or include, but not limited to, a computer/processor 2104 that can include, for example one or more microprocessors, and use instructions stored on a computer-accessible medium (e.g., RAM, ROM, hard drive, or other storage device).

As shown in FIG. 21A, for example a computer-accessible medium 2106 (e.g., as described herein above, a storage device such as a hard disk, floppy disk, memory stick, CD-ROM, RAM, ROM, etc., or a collection thereof) can be provided (e.g., in communication with the processing arrangement 2102). The computer-accessible medium 2106 can contain executable instructions 2108 thereon. In addition, or alternatively, a storage arrangement 2010 can be provided separately from the computer-accessible medium 2006, which can provide the instructions to the processing arrangement 2102 so as to configure the processing arrangement to execute certain exemplary procedures, processes and methods, as described herein above, for example.

Further, the exemplary processing arrangement 2102 can be provided with or include an input/output arrangement 2114, which can include, for example a wired network, a wireless network, the internet, an intranet, a data collection probe, a sensor, etc. As shown in FIG. 21, the exemplary processing arrangement 2102 can be in communication with an exemplary display arrangement 2112, which, according to certain exemplary embodiments of the present disclosure, can be a touch-screen configured for inputting information to the processing arrangement in addition to outputting information from the processing arrangement, for example. Further, the exemplary display 2112 and/or a storage arrangement 2110 can be used to display and/or store data in a user-accessible format and/or user-readable format.

Figure 21B:
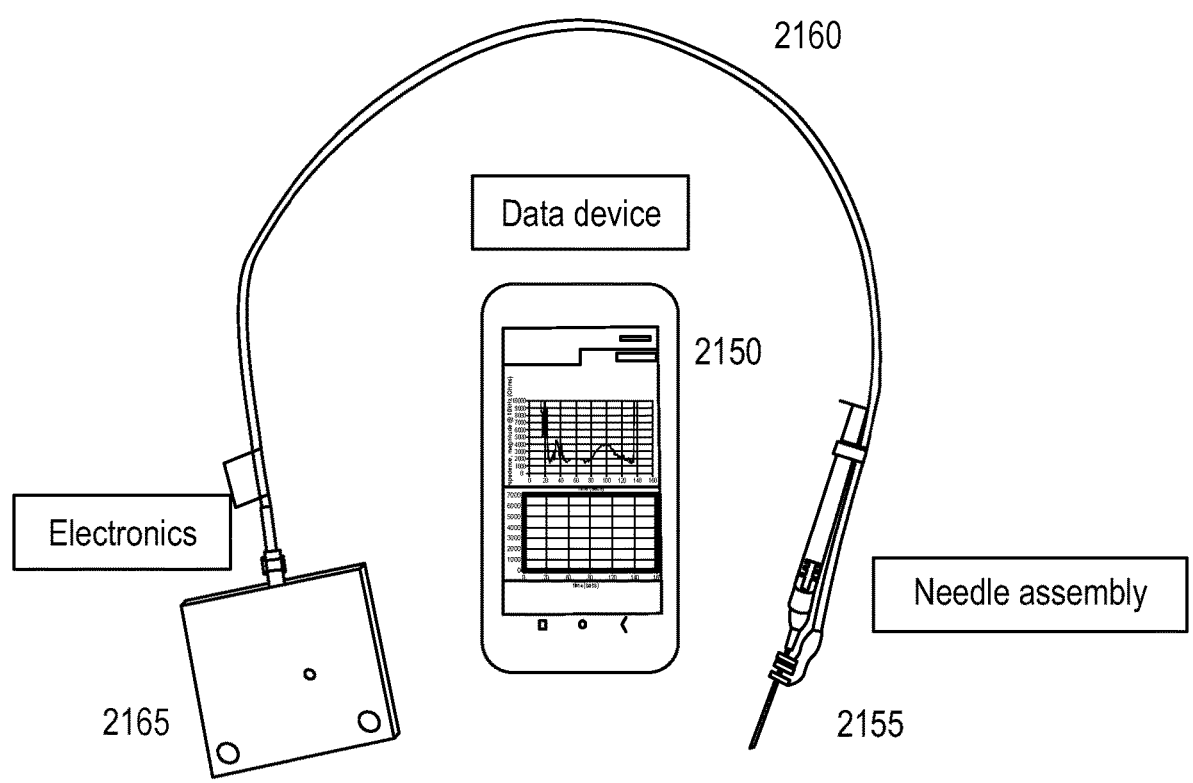
FIG. 21B is an illustration of an exemplary device incorporating the exemplary insertion apparatus tethered to an external electronics package to infer impedance along with a data device connected wirelessly via Bluetooth to a data device which displays and records data, according to an exemplary embodiment of the present disclosure.

FIG. 21B is a photograph of an exemplary embodiment of the exemplary system described herein above with reference to FIG. 21A. For example, the exemplary system incorporates electronics housed in a box which can be a computing device 2150 or a data device, including but not limited a mobile phone, tablet, etc. separate from the exemplary insertion device/apparatus 2160 (various exemplary embodiments described herein) and connected using a coaxial cable 2170 which can be terminated with a connector that can provide an electrical contact with both the outer electrical coating and the hypodermic needle tubing of the exemplary insertion device/apparatus 2160. The electronics incorporate an nRF52840 System-on-Chip (SoC) is used to perform the analog to digital conversion, digital signal processing and wireless communication. The electronics can communicate wirelessly with the computing device 2150 or data device using wireless communication protocol(s), e.g., Bluetooth. The computing device 2150 can receive data, provide a real time display of the measured impedance (both magnitude and angle), and/or record the data.

Figure 21C:
FIG. 21C is an illustration of exemplary data collected during needle insertion into a rabbit femoral vein using a device with external electronics, according to an exemplary embodiment of the present disclosure.
Figure 21C:
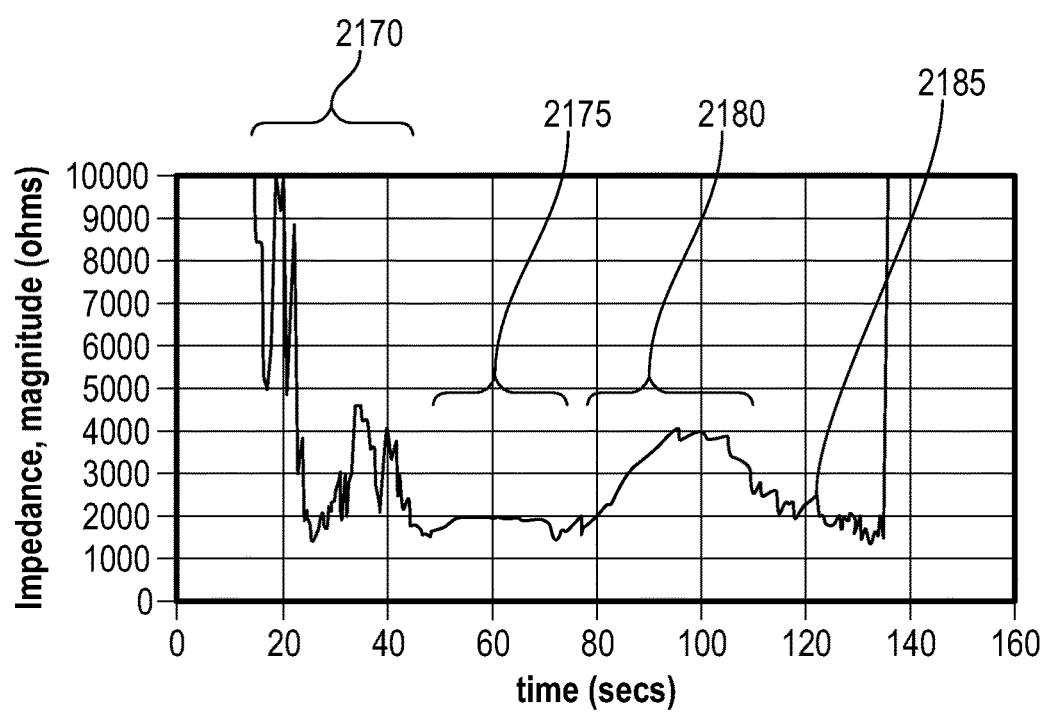

FIG. 21C illustrates a measured response from the system during insertion into the inner thigh of a New Zealand White rabbit. The exemplary insertion apparatus (e.g., a needle—exemplary structures of which is described herein) was inserted through the skin and then guided into the femoral vein which was visible just below the skin. Blood could be seen inside the needle hub, verifying that the needle was inside the vein. The exemplary insertion apparatus was then held in place for several seconds and then advanced through the opposing vein wall into the underlying muscle. Finally, the exemplary insertion apparatus was withdrawn.

As shown in FIG. 21C which illustrates exemplary data, the measured impedance magnitude showed continuous changes as the needle was advanced through tissue and then into the femoral vein. The recorded values remained high, generally above 2,000 Ohms except for a brief time during which the needle may have momentarily contacted a blood vessel. The data for the initial insertion through skin into muscle, possible brief passage through vessel is provided in FIG. 21B for period 2170. As the needle entered the femoral vein (e.g., the needle held stationary), the measured impedance magnitude dropped to a relatively steady value between 1,500 Ohms and 2,000 Ohms for period 2175. As the needle was advanced through the vein and into muscle, the measured impedance magnitude increased above 2,000 Ohms, as provided in period 2180. As the needle was withdrawn, the measured impedance magnitude decreased briefly as the needle tip passed back through the femoral vein and then increased as the needle was pulled out of the leg, as provided in period 2185.

These exemplary results shown in FIG. 21C illustrate how an exemplary system may behave during a clinical application such as injection of a filler. In one example, the user can insert the exemplary insertion apparatus (e.g., needle) into a patients face. A small AC current passes from the hypodermic needle body through tissue or fluid in contact with the tip and then to the outer coating. The electronics infer impedance from the changes in the current caused during passage through the tissue or fluid. During initial insertion, the measured impedance magnitude will remain high. If the needle tip enters a blood vessel in the face, the measured impedance magnitude will show a distinct drop. The electronics may be designed to detect when the measured impedance magnitude is within a defined range, for example, between 1,000 Ohms and 2,000 Ohms. If the measured impedance magnitude is within this exemplary range, the exemplary electronics and/or the exemplary electronic computing device as described herein below can provide, e.g., an alert through the data device, for example an audible tone or a visual cue such as a light. Changes in, e.g., impedance angle or phase may also be used. The user may use the alert as an indication that the needle is in a blood vessel and/or that it may be unsafe to inject a filler.

This exemplary information can be used in other procedures, for example, during phlebotomy procedures, IV line placement, or catheter introduction. The alert or another audio and/or visual indication can be used to let a user know that the needle is inside a vessel and that it is safe to proceed.

Figure 21D:
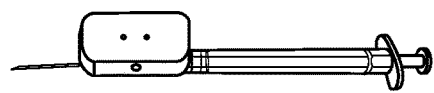
FIG. 21D is an illustration of the operation of an exemplary integrated system using lights to provide information to a user, according to an exemplary embodiment of the present disclosure.
Figure 21D:
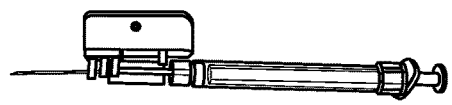
Figure 21D:
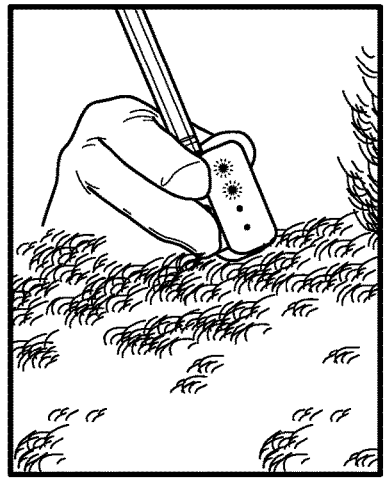
Figure 21D:
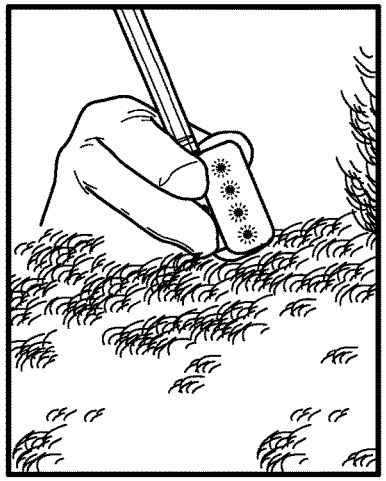
Figure 21D:
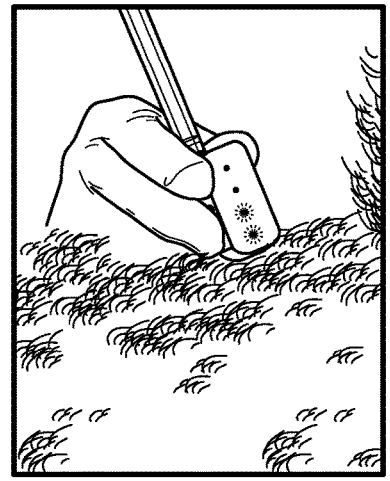

FIG. 21D illustrates a set of photographs of an exemplary embodiment of the exemplary system which integrates the electronics into the exemplary needle using light to provide a user with an alert. The exemplary electronics package clipped onto the exemplary needle making electrical contact with the central needle body as well as the outer conductive coating (image 2191), as described in various exemplary embodiments provided herein. The exemplary electronics shown in FIG. 21D incorporate, e.g., a MSP430FR2355TRHA microcontroller by Texas Instruments. The exemplary microcontroller monitored the measured impedance and detected such measured impedance when the magnitude is below 1,500 Ohms (image 2192), between 1,500 Ohms and 5,000 Ohms (image 2193), and above 5000 Ohms (image 2194). When the impedance is below 1,500 Ohms, one set of LED lights are on as shown in the figure. When the impedance is between 1,500 Ohms, and 5,000 Ohms, both sets of LED lights are on with the intensity of the LED's varying with the magnitude. When the impedance is above 5,000 Ohms, the opposite set of LED lights are on.

For example, FIG. 21D illustrates the exemplary operation during the exemplary needle insertion into a rabbit leg in what is believed to be the femoral vein. For example, when the exemplary needle is inserted into the vessel, one set of lights can be turned on and/or a particular audible signal issued. When the needle is inserted into muscle, both sets of lights are on and/or another audible signal issued. When the needle is in tissue with higher impedance, the opposite set of lights are on and/or still another audible signal issued.

It should be understood that the same or similar function can be achieved with a different number of lights or even with a single light with varying intensity, as well as various sounds, as well as or instead of a combination of light(s) and sounds. It should also be understood that the exemplary instructions used to adjust the light can be adjusted to monitor for values below or above a particular threshold and/or within a particular range or following a particular sequence.

EXAMPLES

Example 1. Impedance Phase Angle Defines Tissue Type

Figure 12A:
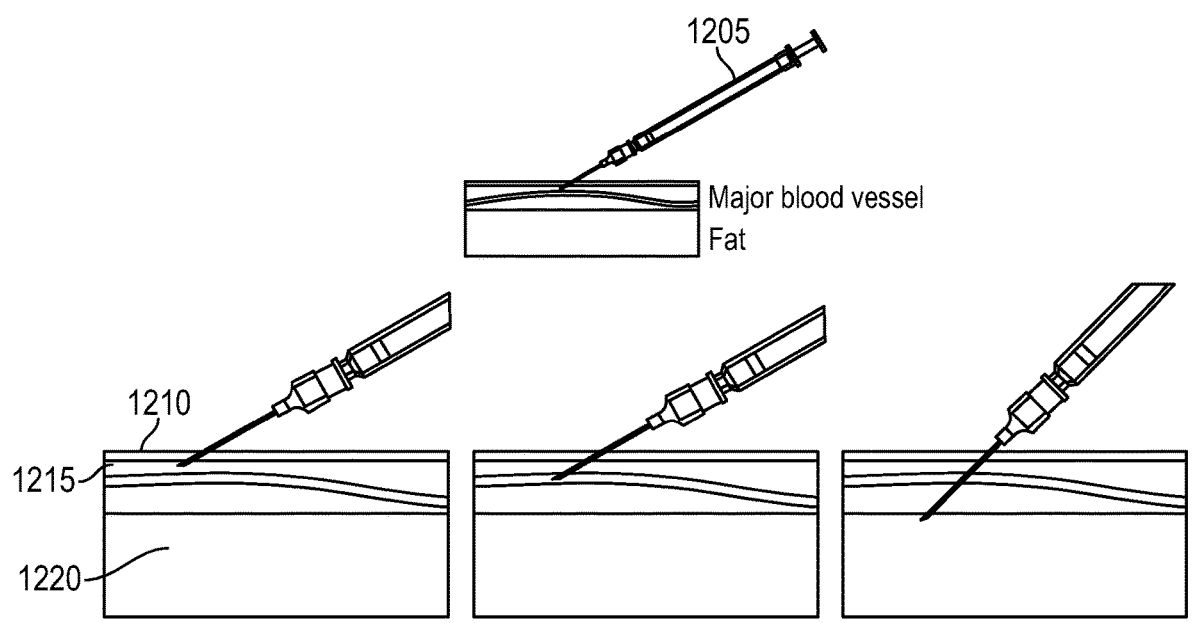
FIG. 12A is a set of exemplary illustrations showing the exemplary insertion device/apparatus inserted into different tissue types according to an exemplary embodiment of the present disclosure.

In-vivo testing was performed using fully integrated electrodes produced according to the pad printing procedure described above (see FIGS. 6 and 7). Testing was performed in a live New Zealand White rabbit to measure impedance in several different types of tissue. A cutdown was performed to expose major blood vessels in the rabbit's neck and thigh. Needles were inserted into different tissues to different depths. Magnet wire was used to connect the electrodes to an impedance analyzer (e.g., Keysight 4294A/1D5). Measured impedance (e.g., magnitude and angle) was exported to text files. FIG. 12A shows a set of exemplary diagrams and side views illustrating exemplary needle 1205 inserted into different tissue types according to an exemplary embodiment of the present disclosure. The tissue types included dermis 1210, major blood vessels 1215, and fat 1220.

Figure 12B:
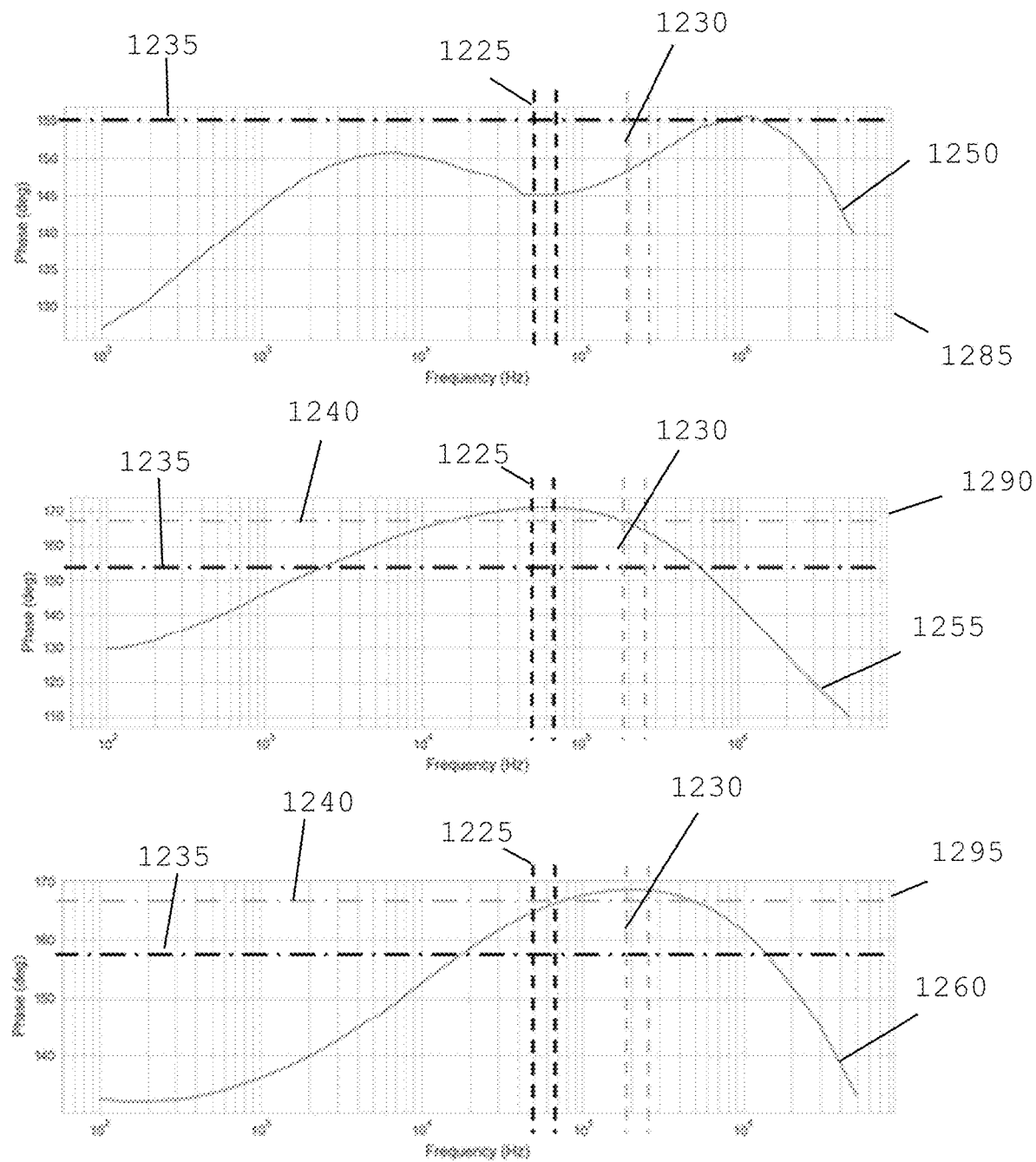
FIG. 12B is a set of exemplary graphs illustrating the impedance phase angle obtained as a function of frequency with the tip of the insertion device/apparatus inserted into different types of tissues according to an exemplary embodiment of the present disclosure.
Figure 15:
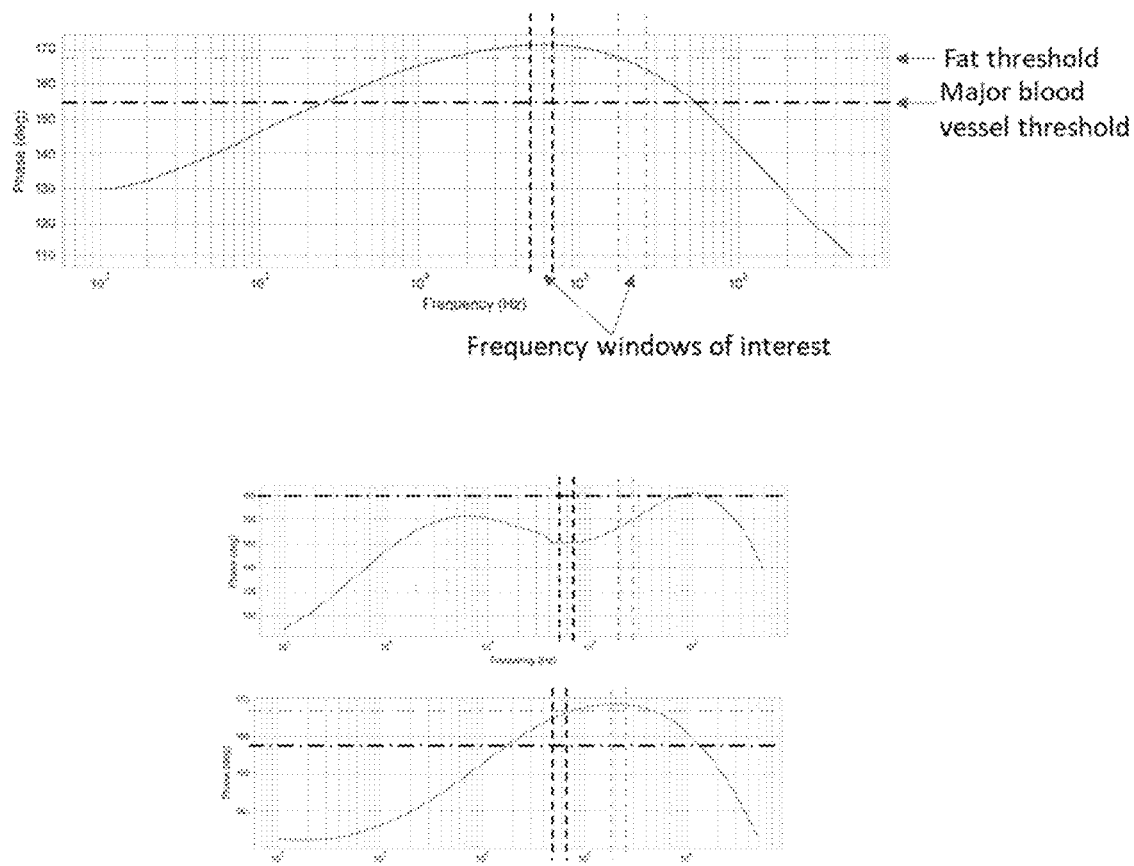
FIGS. 15-18B are exemplary graphs showing exemplary results obtained using the exemplary insertion device/apparatus according to an exemplary embodiment of the present disclosure.

FIG. 12B shows a set of exemplary graphs illustrating the impedance phase angle obtained as a function of frequency with the tip of the needle inserted into different types of tissues according to an exemplary embodiment of the present disclosure. The impedance phase angle was obtained as a function of frequency with the tip of the needle inserted into different types of tissues including dermis 1285, jugular vein 1255, and fat 1925. As shown in the graphs of FIG. 12B, the measured phase angle varies with frequency. Dashed vertical lines and dashed horizontal lines superimposed onto the graphs are provided for reference and represent discrete frequency bands and phase angle thresholds that can be used for an exemplary sensing procedure. Dark vertical lines 1225 represent a band of frequencies from 50 kHz and 65 kHz. Lighter vertical lines 1230 represent a band of frequencies from 190 kHz to 250 kHz. Dark horizontal lines 1235 are placed at 158°. Light horizontal lines 1240 are placed at 167 degrees. As shown in graph 1285, when the exemplary needle is inserted into skin, the measured phase angle 1250 remains below both dark vertical lines 1225 and light vertical lines 1230 at all frequencies. As shown in graph 1290, when the exemplary needle is inserted into the jugular vein, the measured phase angle 1255 exceeds the threshold defined by light horizontal line 1240 in the lower band of frequencies. As shown in graph 1925, when the exemplary needle is inserted into fat, the measured phase angle 1260 exceeds the threshold defined by the light horizontal line in the higher band of frequencies. The exemplary graphs shown in FIG. 15 indicate that it is possible to set thresholds for phase angle in a specific, narrow band of frequencies to detect the difference between different types of tissue.

Example 2. Impedance Magnitude Defines Tissue Type

Figure 16:
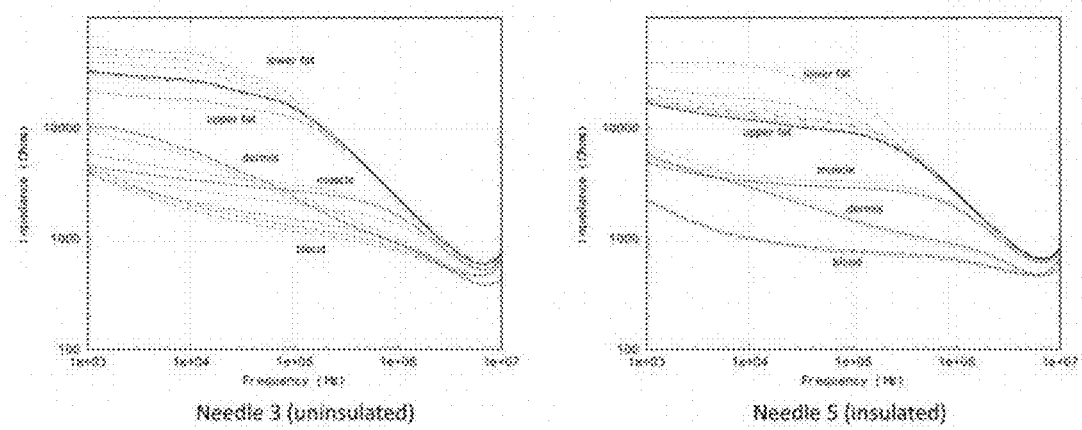
Figure 17:
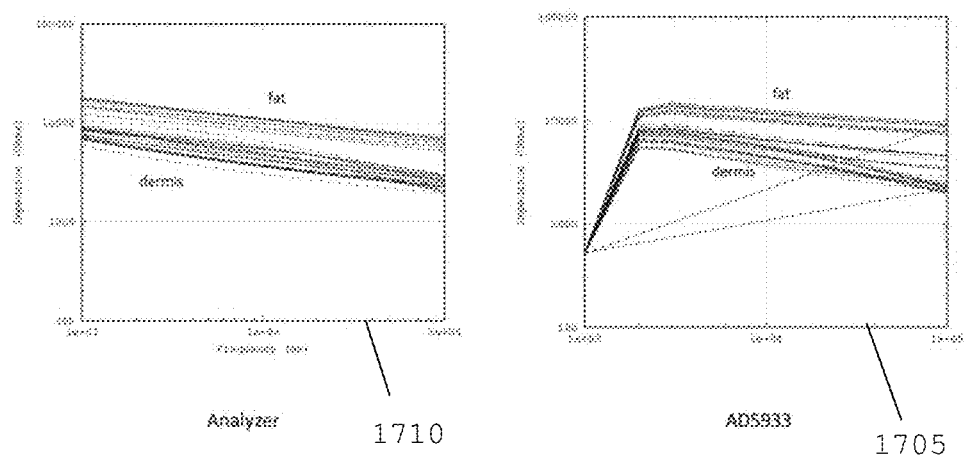
Figure 18A:
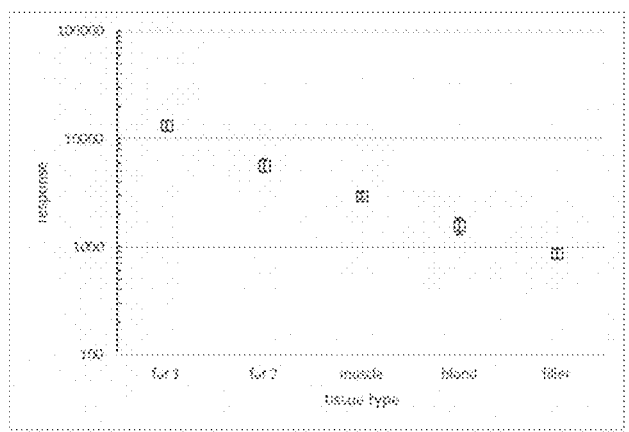
Figure 18B:
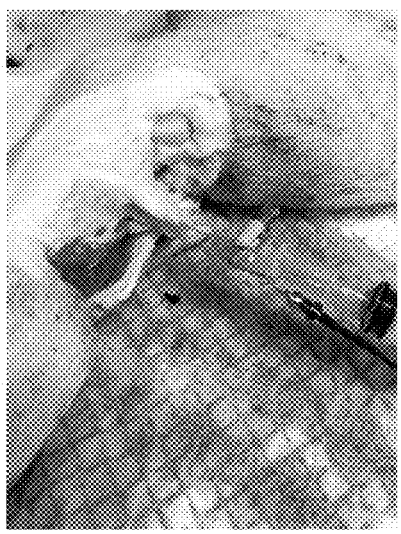
Figure 18B:
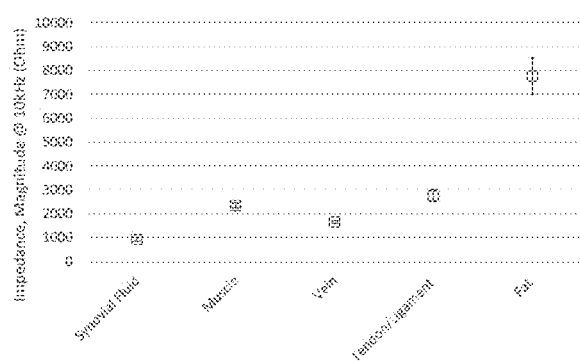

FIGS. 16-18 shows graphs illustrating exemplary results obtained using the exemplary insertion device/apparatus according to an exemplary embodiment of the present disclosure. The exemplary insertion device/apparatus was inserted into different types of fresh tissue harvested from a pig and spectra of the measured magnitude and phase angle were collected using an impedance analyzer. The exemplary graphs shown in FIG. 16 illustrate clear differentiation between the measured impedance magnitude response in various tissue as a function of frequency. Exemplary results showed a variation in response in different tissues at different frequencies. The presence of an outer layer of PET heat shrink on the outside of the needles had little effect on the relative response. Frequencies that illustrate clear differences between the measurements obtained for different tissues can be beneficial. These frequencies can vary depending on the target tissue. Results indicate that 1,000 Hz and 10,000 Hz provide sufficient response to differentiate fat from skin/muscle as there is a difference between the impedance measured in fat vs the measurements from other tissue types. The graphs illustrated in FIG. 17 illustrate that the exemplary impedance measured over a very limited range, 1,000 Hz and 10,000 Hz can provide sufficient response to differentiate skin, fat, muscle, and that a single chip solution can provide comparable relative responses to an analyzer. Exemplary results shown in graph 1705 were obtained using an exemplary impedance measurement chip while the results shown in graph 1710 were obtained using a laboratory analyzer.

FIG. 18A shows an exemplary graph comparing the variation in impedance magnitude obtained in a live Yucatan pig with exemplary electronics at a single frequency, 10,000 Hz. Each symbol represents the pooled mean result obtained from multiple continuous measurements. This same data is tabulated in Table 1. The needle was removed and then reinserted after each measurement. Error bars represent the range above and below the mean from two times the standard deviation, a based on the pooled measurements. As there was no overlap of the results measured from fat as compared to dermis and muscle, this indicates that the exemplary needle system can sense the difference between fat and dermis/muscle using measured impedance magnitude obtained from both instruments. Further, results indicate that measurements obtained at a single frequency, e.g., 10,000 Hz can be sufficient to resolve fat vs. dermis or muscle. Measured impedance magnitude can be pooled to obtain mean and standard deviations for tissue and fluid types believed to correspond to measurements. Mean values are shown using square markers. Standard deviations are illustrated with error bars.

TABLE 1

Combination of all results correlating to different tissues and fluids measured during in-vivo testing in a Yucatan pig provided pooled estimates for impedance magnitude

| Tissue Type | Mean (ohms) | Std Dev (ohms) |
| --- | --- | --- |
| Fat 1 | 13441.19 | 1332.923 |
| Fat 2 | 5692.242 | 810.7929 |
| Muscle | 2983.11 | 204.831 |
| Blood | 1576.659 | 268.8275 |
| Filler | 866.0706 | 81.88926 |

FIG. 18B shows an exemplary graph of the measured impedance magnitude obtained from testing performed in a freshly excised Yorkshire pig leg, specifically tissue and fluid in and around the stifle joint which is roughly equivalent to a human knee. Data was collected using an exemplary system at a single frequency, 10,000 Hz. Each symbol represents the mean result obtained from multiple measurements. This same data is tabulated in Table 2. The needle was removed and then reinserted after each measurement. Error bars represent the range above and below the mean from three times the standard deviation, σ based on the pooled measurements. For a normal data set, the 3σ range contains approximately 99.7% of the values. (See, e.g., Reference 7).

TABLE 2

Mean measured impedance magnitude collected from different tissues and fluids measured during in-vitro testing in a freshly harvested Yorkshire pig. 3x standard deviation also provided as an indication of scatter

| Tissue Type | Mean (ohms) | Std Dev (ohms) |
| --- | --- | --- |
| Synovial Fluid | 921 | 72 |
| Muscle | 2346 | 104 |
| Vein | 165 | 55 |
| Tendon/Ligament | 2759 | 252 |
| Fat | 7767 | 763 |

Based on the exemplary data including, but not limited to, the data described and/or incorporated herein, an exemplary device and/or system can monitor the measured impedance magnitude for values within specific ranges to infer different tissue types or fluids. For the 26 Ga RW needle coated with a 0.001 in thick layer of polyimide and with an outer coating of 0.001 in thick silver filled ink used to measure the data, the ranges of impedance magnitude are included in Table 3.

TABLE 3

Range of Exemplary Impedance Magnitudes in Tissue/Fluid

| Tissue/Fluid Type | Impedance Magnitude (Ohms) |
| --- | --- |
| Whole Blood | 1,000 Ohms to 2,000 Ohms |
| Muscle | 2,000 Ohms to 5,000 Ohms |
| Fat | 5,000 Ohms to 40,000 Ohms |
| Synovial Fluid | 200 Ohms to 1,000 Ohms |

In addition to the specific needle size and materials, these are results specific to one frequency, 10,000 Hz and one specific needle point.

A person of skill in the art would recognize that changes to an exemplary needle geometry lead to a reduction in the measured impedance magnitude. An increase in the needle gage or size increases the sensing area and the amount of tissue in contact with the needle. For a fixed voltage, more electrical current will appear to pass through the tissue, following Ohm's law. This will decrease the measured impedance magnitude with a linear change tied to the change in the circumference of the needle. Increasing the thickness of the insulating area will increase the distance that the electrical current must pass through hence, increasing the amount of tissue in the electrical path. This will lead to a decrease in the measured impedance magnitude which will be linearly proportional to the change in thickness. Similarly, a change in the needle point will lead to a change in geometry, which will affect the measured impedance magnitude. For example, decreasing the primary grind produces a point with a shallower angle. Based on geometry, this increases the effective distance that electrical current must travel and increases the amount of tissue that that the current must pass through. This can increase or decrease the measured impedance magnitude. A skilled practitioner would also recognize that a change in the frequency may also alter the measured impedance magnitude or phase as a change in frequency will change the relative contributions of the resistance and reactance. Accordingly, depending on the features of the exemplary device, the range of impedance magnitude per tissue or fluid type can be readily determined by a skilled practitioner according to the methods of the invention described herein.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

[1] Kai Kronström, Petri Ahonen, Sanna MÄKI, Timo Elomaa, Juho Kari, US 2018/0296197 A1, Biopsy Needle For Biopsy Sampling, Biopsy Device, And Methods Of Manufacturing A Biopsy Needle Or A Biopsy Device.
[2] Kai Kronstrom, Petri Ahonen, Juho Kari, Riitta Seppanen, US 2016/0029920 A1, Bioimpedance Sensor, Stylet, Cannula And Method For Measuring Biompedance.
[3] Joho Yun, Jinhwan Kim, Jong-Hyun Lee, "Fabrication of Fine Electrodes on the Tip of Hypodermic Needle Using Photoresist Spray Coating and Flexible Photomask for Biomedical," Journal of Visualized Experiments, November 2017|129|e56622|.
[4] Joho Yun, Hyeon Woo Kim, Yangkyu Park, Jung-Joon Cha, Jeong Zoo Lee, Dong Gil Shin, and Jong-Hyun Lee, Micro electrical impedance spectroscopy on a needle for ex vivo discrimination between human normal and cancer renal tissues, Biomicrofluidics 10, 034109 (2016).
[5] Ivorra Cano, Antoni, Contributions to the measurement of electrical impedance for living tissue ischemia injury monitoring, Doctoral Thesis, Universitat Politècnica de Catalunya, 2005.
[6] Mohammed H. Abduljabbar, Mohammad A. Basendwh. "Complications of hyaluronic acid fillers and their managements," Journal of Dermatology & Dermatologic Surgery 20 (2016) 100-106
[7] Wheeler, D. J. et al., Statistical Tolerance Intervals (1992). Understanding Statistical Process Control. Quality Digest, pgs. 1-13 [From the Internet] https://www.qualitydigest.com/inside/statistics-column/stattistical-tolerance-intervals-010416.html
[8] Covidien, "Principles of Electrosurgery," Boulder Colo., 2008.
[9] Rocha, Rafael Dahmer, Pinto, Renata Reis, Tavares, Diogo Paes Barreto Aquino, Gonçalves, Cláudia Sofia Aires, "Step-by-step of ultrasound-guided core-needle biopsy of the breast: review and technique," Radiol Bras. 2013 July/Ago; 46(4):234-241.

What is claimed is:

1. An insertion apparatus, comprising:
a first electrically conductive layer circumferentially surrounding a lumen;
an insulating layer (i) at least partially surrounding the first electrically conductive layer, and (ii) at least one of spray coated, electrochemically deposited, vapor deposited or sputtered on the first electrically conductive layer;
a second electrically conductive layer at least partially surrounding the insulating layer, and
an electrical connector,
wherein the insulating layer electrically isolates the first electrically conductive layer from the second electrically conductive layer,
wherein the first electrically conductive layer has a portion with an outer surface that (i) faces away from the lumen, and (ii) is externally uncovered by the insulating layer and the second electrically conductive layer,
wherein the outer surface of the portion of the first electrically conductive layer is integrally provided with the electrical connector which extends radially outward and provides an electrical connection to the insertion apparatus,
wherein the electrical connector (i) has a terminal end, and (ii) is unconnected to the rest of the insertion apparatus, and
wherein the second electrically conductive layer covers the insulating layer at a most distal pointed terminal end of the insertion apparatus.

2. The insertion apparatus of claim 1, wherein the first electrically conductive layer, the insulating layer, and the second electrically conductive layer form a structure which has a first side and a second side disposed opposite to the first side with respect to the lumen, and wherein the first side is longer than the second side thereby forming the most distal pointed terminal end which is a sharp pointed end via the first side at a distal-most portion of the insertion apparatus.

3. The insertion apparatus of claim 1, wherein the first electrically conductive layer, the insulating layer, and the second electrically conductive layer form a beveled structure that has a distal-most grinded end forming the most distal pointed terminal end which is a grinded sharp pointed end at a distal-most portion of the insertion apparatus, and wherein the outer surface of the portion of the first electrically conductive layer is provided on a proximal-most portion of the insertion apparatus.

4. The insertion apparatus of claim 1, wherein the first electrically conductive layer, the insulating layer, and the second electrically conductive layer form a shaft of the insertion apparatus.

5. The insertion apparatus of claim 4, further comprising a hub, wherein the shaft extends distally from the hub, and wherein a section of the outer surface of the portion of the first electrically conductive layer is provided adjacent to the hub.

6. The insertion apparatus of claim 5, further comprising:
a barrel connected to the hub; and
a plunger configured to be inserted into the barrel.

7. The insertion apparatus of claim 1, wherein the first electrically conductive layer is configured to obtain a first electrical signal, and the second electrically conductive layer is configured to obtain a second electrical signal, and further comprising at least one communication device configured transmit information related to the first and second electrical signals.

8. The insertion apparatus of claim 7, wherein the at least one communication device is embedded in one of (i) a hub proximal to a shaft formed by the first electrically conductive layer, the insulating layer, and the second electrically conductive layer, or (ii) a barrel connected to the hub.

9. The insertion apparatus of claim 1, wherein the first electrically conductive layer is configured to obtain a first electrical signal, and the second electrically conductive layer is configured to obtain a second electrical signal, further comprising a computer hardware arrangement configured to:
receive information related to the first and second electrical signals;
determine an impedance based on the information; and
determine a tissue type based on the impedance.

10. The insertion apparatus of claim 9, further comprising at least one audible arrangement configured to emit a sound based on the determined tissue type.

11. The insertion apparatus of claim 9, wherein the processing arrangement is embedded in one of (i) a hub proximal to a shaft formed by the first electrically conductive layer, the insulating layer, and the second electrically conductive layer, or (ii) a barrel connected to the hub.

12. The insertion apparatus of claim 9, wherein, upon the determination of the tissue type of a specific tissue that is of interest, at least one current is provided to at least one of the first electrically conductive layer or the second electrically conductive layer so as to generate an energy field detectable by signals detectors which transmit location information of at least one portion of the insertion apparatus to the computer hardware arrangement.

13. The insertion apparatus of claim 12, wherein the signal detectors include at least two antennas.

14. The insertion apparatus of claim 12, wherein the computer hardware arrangement is further configured to determine a three-dimensional location of the at least one portion of the insertion apparatus at or in a body based on the location information.

15. The insertion apparatus of claim 12, wherein the computer hardware arrangement is further configured to generate an image on a display of the at least one portion of the insertion apparatus at or in a body in a three-dimensional space based on the location information.

16. The insertion apparatus of claim 1, wherein the lumen is configured to at least one of (i) have a pharmacological agent injected therethrough, or (ii) have a biopsy obtained therethrough.

17. The insertion apparatus according to claim 1, wherein the electrical connector is integrally provided with the outer surface of the portion of the first electrically-conductive layer at a proximal section of the insertion apparatus, and wherein the second electrically conductive layer extends to a distal-most edge of a distal section of the insertion apparatus.

18. The insertion apparatus according to claim 1, wherein the electrical connector is configured to be connected to at least one of (i) one or more wires, (ii) a flex circuit or (iii) a cable so as to connect to an external device.

19. The insertion apparatus according to claim 1, wherein the first electrically conductive layer is configured to transmit an electrical signal, and wherein the second electrically conductive layer is configured to receive the electrical signal, wherein a computer arrangement is connected to the insertion arrangement, and is configured to determine information regarding at least one tissue or an orifice of at least one tissue of a subject by using an impedance that is based on the electrical signal.

20. An insertion apparatus, comprising:
a hub;
an electrical connector; and
a shaft extending from the hub and surrounding a lumen, wherein the shaft includes an outer surface having at least one first electrode formed thereon or therein, wherein the at least one first electrode extends for more than half of an external circumference of the shaft, wherein the shaft includes:
at least one second electrode formed or provided on or in an inner surface thereof, and
an insulator (i) separating and insulating the first and second electrodes from one another, and (ii) at least one of spray coated, electrochemically deposited, vapor deposited or sputtered on the second electrode,
wherein the at least one second electrode has an outer portion with an outer surface that (i) faces away from the lumen, and (ii) is not covered externally by the insulator,
wherein the outer surface of the outer portion of the at least one second electrode is integrally provided with the electrical connector which extends radially outward and provides an electrical connection to the insertion apparatus,
wherein the electrical connector (i) has a terminal end, and (ii) is unconnected to the rest of the insertion apparatus, and
wherein the first electrode covers the insulator at a most distal pointed terminal end of the insertion apparatus.

21. The insertion apparatus of claim 20, further comprising:
a barrel connected to the hub; and
a plunger configured to be inserted into the barrel.

22. The insertion apparatus according to claim 20, wherein the electrical connector is configured to be connected to at least one of (i) one or more wires, (ii) a flex circuit or (iii) a cable so as to connect to an external device.

23. The insertion apparatus according to claim 20, wherein the at least one first electrode is configured to transmit an electrical signal, and wherein the at least one second electrode is configured to receive the electrical signal, wherein a computer arrangement is connected to the insertion arrangement, and is configured to determine information regarding at least one tissue or an orifice of at least one tissue of a subject by using an impedance that is based on the electrical signal.

24. A method for determining information regarding at least one tissue of a subject or an orifice of the at least one tissue using an insertion arrangement, comprising:
introducing the insertion arrangement into at least one target site of the subject to reach the at least one tissue;
transmitting an electrical signal using a first electrically conductive layer of the insertion arrangement that at least partially surrounds a lumen of the insertion arrangement;
receiving the electrical signal using a second electrically conductive layer of the insertion arrangement that at least partially surrounds an insulating layer which at least partially surrounds the first electrically conductive layer;
providing the electrical signal from an external source via an electrical connector that extends radially outward and is integrally provided with an outer surface of a portion of the first electrically conductive layer that (i) faces away from the lumen, and (ii) is externally uncovered by the insulating layer and the second electrically conductive layer, wherein the electrical connector (i) has a terminal end, and (ii) is unconnected to the rest of the insertion arrangement; and
determining an impedance based on the electrical signal, thereby determining the information regarding the at least one tissue or the orifice of the at least one tissue of the subject.

25. The method of claim 24, wherein the outer surface of the portion of the first electrically conductive layer is provided on a proximal-most portion of the insertion arrangement.

26. The method of claim 24, further comprising at least one of (i) administering a pharmacological agent to the subject through the lumen, or (ii) obtaining a biopsy sample from the subject through the lumen.

27. The method of claim 24, wherein the at least one tissue is muscle or fat.

28. The method of claim 24, further comprising determining whether a particular type of tissue or the orifice of the at least one tissue has been reached based on the impedance, and based on the determination of whether the type or the orifice of the at least one tissue has been reached, providing at least one current to at least one of the first electrically conductive layer or the second electrically conductive layer so as to generate an energy field detectable by signals detectors which transmit location information of at least one portion of the insertion apparatus to a computer hardware arrangement.

29. The method of claim 28, further comprising determining a three-dimensional location of the at least one portion of the insertion apparatus at or in a body based on the location information.

30. The method of claim 28, further comprising generating an image on a display of the at least one portion of the insertion apparatus at or in a body in a three-dimensional space based on the location information.

31. The method according to claim 24, wherein the electrical connector is configured to be connected to at least one of (i) one or more wires, (ii) a flex circuit or (iii) a cable so as to connect to the external source.

32. The method according to claim 24, wherein the insulating layer is at least one of spray coated, electrochemically deposited, vapor deposited or sputtered on the first electrically conductive layer, and wherein the second electrically conductive layer covers the insulating layer at a most distal pointed terminal end of the insertion arrangement.

33. A hollow tubular structure, comprising:
a first electrically conductive layer circumferentially surrounding a lumen;
an insulating layer (i) at least partially surrounding the first electrically conductive layer, and (ii) at least one of spray coated, electrochemically deposited, vapor deposited or sputtered on the first electrically conductive layer;
a second electrically conductive layer at least partially surrounding the insulating layer, and
an electrical connector,
wherein the first and second electrically conductive layers, the insulating layer and the electrical connector are provided in a fixed manner,
wherein the insulating layer electrically isolates the first electrically conductive layer from the second electrically conductive layer,
wherein the first electrically conductive layer has a portion with an outer surface that (i) faces away from the lumen, and (ii) is externally uncovered by the insulating layer and the second electrically conductive layer,
wherein the outer surface of the portion of the first electrically conductive layer is integrally provided with the electrical connector which extends radially outward and provides an electrical connection to the hollow tubular structure,
wherein the electrical connector (i) has a terminal end, and (ii) is unconnected to the rest of the hollow tubular structure, and
wherein the second electrically conductive layer covers the insulating layer at a most distal pointed terminal end of the tubular structure.

34. The hollow tubular structure according to claim 33, wherein the electrical connector is configured to be connected to at least one of (i) one or more wires, (ii) a flex circuit or (iii) a cable so as to connect to an external device.

35. The hollow tubular structure according to claim 33, wherein the first electrically conductive layer is configured to transmit an electrical signal, wherein the second electrically conductive layer is configured to receive the electrical signal, and wherein the hollow tubular structure is connected to a computer arrangement which configured to determine information regarding at least one tissue or an orifice of at least one tissue of a subject by using an impedance that is based on the electrical signal.

\* \* \* \* \*